United States Patent
Alarcon et al.

(10) Patent No.: US 10,034,495 B2
(45) Date of Patent: Jul. 31, 2018

(54) DEVICE FOR STORING AND VAPORIZING LIQUID

(71) Applicant: Fontem Holdings 1 B.V., Amsterdam (NL)

(72) Inventors: Ramon Alarcon, Los Gatos, CA (US); Dennis Rasmussen, Campbell, CA (US); Christopher Myles, San Jose, CA (US)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 0 days.

(21) Appl. No.: 15/219,218

(22) Filed: Jul. 25, 2016

(65) Prior Publication Data
US 2018/0020730 A1    Jan. 25, 2018

(51) Int. Cl.
| H05B 3/06 | (2006.01) |
| A24F 47/00 | (2006.01) |
| F16K 15/04 | (2006.01) |
| A61M 15/06 | (2006.01) |
| A61M 11/04 | (2006.01) |
| A61M 15/00 | (2006.01) |
| A61M 11/00 | (2006.01) |
| A61M 16/00 | (2006.01) |

(52) U.S. Cl.
CPC ......... *A24F 47/008* (2013.01); *A61M 11/042* (2014.02); *A61M 15/0015* (2014.02); *A61M 15/06* (2013.01); *F16K 15/04* (2013.01); *H05B 3/06* (2013.01); *A61M 11/005* (2013.01); *A61M 2016/0024* (2013.01); *A61M 2205/587* (2013.01); *A61M 2205/8206* (2013.01)

(58) Field of Classification Search
CPC ........ A24F 47/008; A24F 15/12; A24F 15/18; F16K 15/04; H05B 3/06
USPC .................................................. 131/329, 347
See application file for complete search history.

(56) References Cited

U.S. PATENT DOCUMENTS

| 5,331,979 | A | 7/1994 | Henley | |
| 8,978,663 | B2 * | 3/2015 | Newton | A24F 47/008 131/347 |
| 9,095,174 | B2 | 8/2015 | Capuano | |
| 2013/0199528 | A1 * | 8/2013 | Goodman | F22B 1/282 128/203.26 |

(Continued)

FOREIGN PATENT DOCUMENTS

| CN | 201054977 Y | 5/2008 |
| CN | 202172846 U | 3/2012 |

(Continued)

*Primary Examiner* — Edwin A. Leon
(74) *Attorney, Agent, or Firm* — Dykema Gossett PLLC

(57) ABSTRACT

In accordance with one aspect of the present invention there is provided an electronic smoking device, having an outer tube mounted around at least a portion of an inner tube. The outer tube can have an outer surface and an inner surface. The inner tube can have an inner surface defining an air path and an outer surface. An annular liquid storage tank is defined between the outer surface of the inner tube and the inner surface of the outer tube. A heater enclosure can define a heater coil chamber. A heater coil can be mounted at least partially within the heater enclosure. A wick can include a first end portion. The wick can extend through a center of the heater coil and the first end portion can extend into a first wick bore in a first wall of the heater enclosure.

17 Claims, 12 Drawing Sheets

(56) References Cited

U.S. PATENT DOCUMENTS

| | | | |
|---|---|---|---|
| 2013/0327327 A1 | 12/2013 | Edwards et al. | |
| 2014/0261486 A1* | 9/2014 | Potter | A24F 47/008 131/328 |
| 2014/0261491 A1 | 9/2014 | Hawes | |
| 2015/0083147 A1* | 3/2015 | Schiff | A24F 47/008 131/329 |
| 2015/0157054 A1 | 6/2015 | Liu | |
| 2015/0313282 A1* | 11/2015 | Ademe | B25F 1/00 131/329 |
| 2015/0335071 A1 | 11/2015 | Brinkley et al. | |
| 2015/0335074 A1 | 11/2015 | Leung | |
| 2016/0095355 A1 | 4/2016 | Hearn | |
| 2016/0150824 A1 | 6/2016 | Memari et al. | |
| 2016/0205998 A1 | 7/2016 | Matsumoto et al. | |
| 2016/0270446 A1 | 9/2016 | Shenkal et al. | |

FOREIGN PATENT DOCUMENTS

| | | |
|---|---|---|
| CN | 104106842 A | 10/2014 |
| CN | 104783327 A | 7/2015 |
| CN | 105581376 A | 5/2016 |
| EP | 2835063 A1 | 6/2013 |
| EP | 3130237 A1 | 2/2017 |
| WO | 2014066730 A1 | 5/2014 |
| WO | 2014199232 A1 | 12/2014 |
| WO | 2015054885 A1 | 4/2015 |
| WO | 2016029225 A1 | 2/2016 |
| WO | 2016055653 A1 | 4/2016 |
| WO | 2016092261 A1 | 6/2016 |

\* cited by examiner

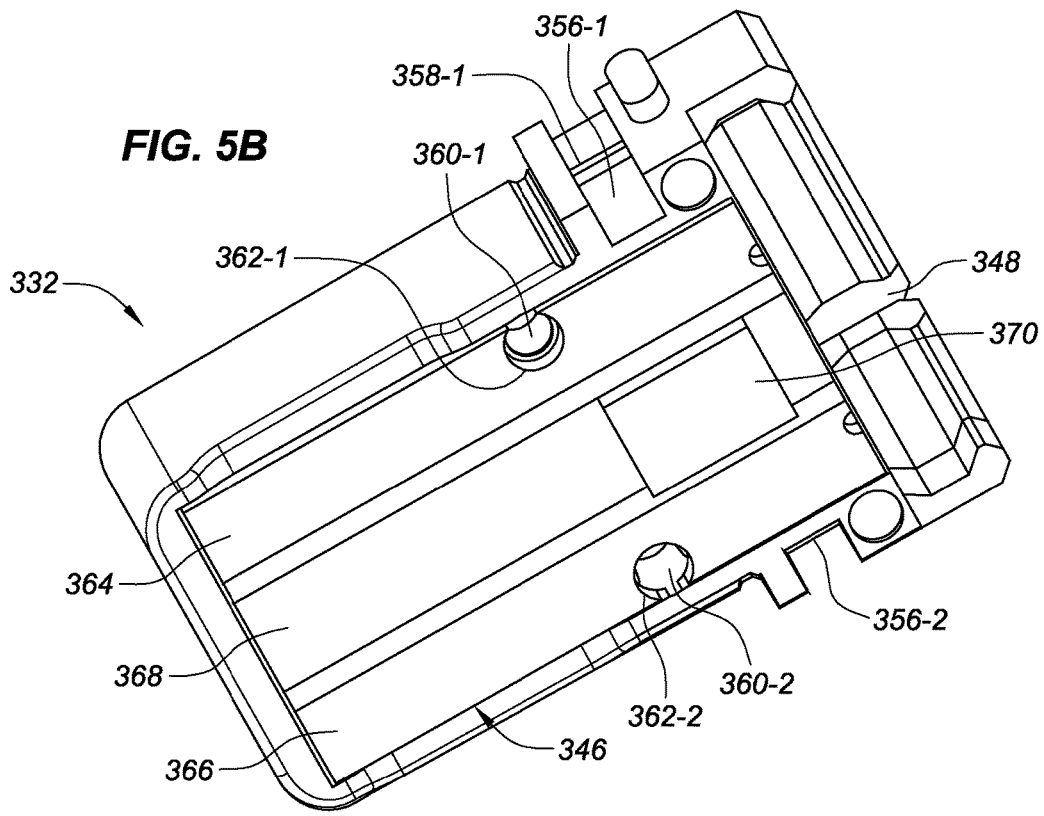
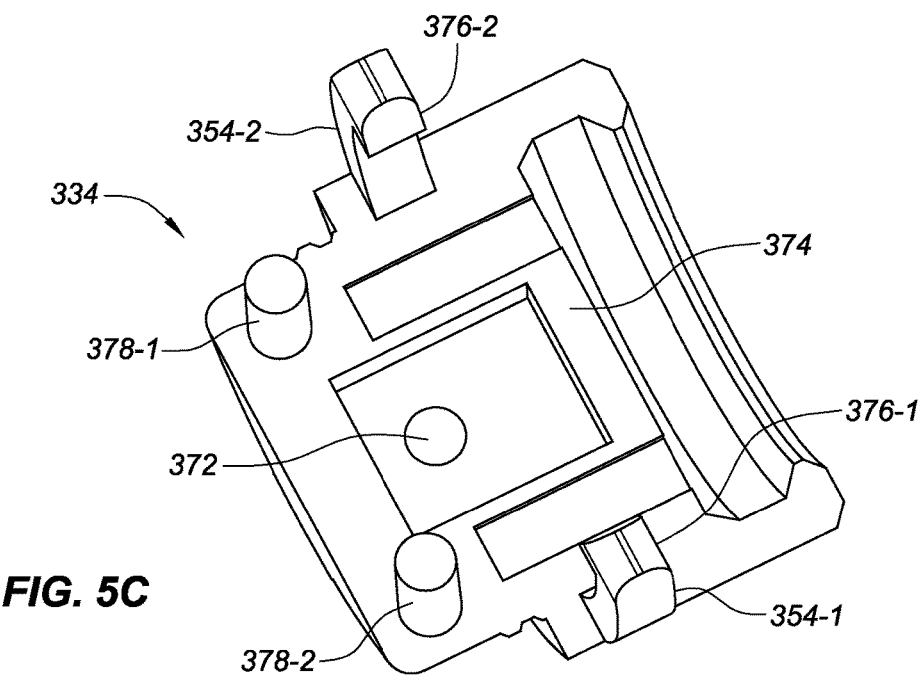

DEVICE FOR STORING AND VAPORIZING LIQUID

FIELD OF INVENTION

The present invention relates generally to electronic smoking devices and in particular electronic cigarettes.

BACKGROUND OF THE INVENTION

An electronic smoking device, such as an electronic cigarette (e-cigarette), typically has a housing accommodating an electric power source (e.g., a single use or rechargeable battery, electrical plug, or other power source), and an electrically operable atomizer. The atomizer vaporizes or atomizes liquid supplied from a reservoir and provides vaporized or atomized liquid as an aerosol. Control electronics control the activation of the atomizer. In some electronic cigarettes, an airflow sensor is provided within the electronic smoking device, which detects a user puffing on the device (e.g., by sensing an under-pressure or an airflow pattern through the device). The airflow sensor indicates or signals the puff to the control electronics to power up the device and generate vapor. In other e-cigarettes, a switch is used to power up the e-cigarette to generate a puff of vapor.

Generally, the reservoir can include a porous media that can store the liquid, which can be drawn to the electrically operable atomizer, such as a heated coil. Upon contact between the liquid and the atomizer, the liquid can be atomized to form a vapor that is inhaled by the user. As liquid stored in the reservoir is used up, liquid that is stored within a close proximity to the atomizer can be wicked from the porous media. In contrast, liquid stored in the porous material at a further proximity to the atomizer may not be wicked to the atomizer because the liquid has to travel a further distance through the porous media. As a result, the amount of liquid media wicked to the atomizer may decrease even when additional liquid is stored in the porous media. This can cause a user of the e-cigarette to experience a drop-off in the "quality" of their experience, because less vapor is produced by the atomizer. This can give the user an impression that the porous media has been depleted of remaining liquid, causing the user to discard the porous media when some amount of liquid remains.

SUMMARY OF THE INVENTION

In accordance with one aspect of the present invention there is provided an electronic smoking device, comprising an outer tube mounted around at least a portion of an inner tube. The outer tube can comprise an outer surface and an inner surface. The inner tube can comprise an inner surface defining an air path and an outer surface. An annular liquid storage tank is defined between the outer surface of the inner tube and the inner surface of the outer tube. A mouth piece is connected to a proximal end of the inner tube and to the outer tube. A heater enclosure can define a heater coil chamber. A heater coil can be mounted at least partially within the heater enclosure. A wick can include a first end portion. The wick can extend through a center of the heater coil and the first end portion can extend into a first wick bore in a first wall of the heater enclosure. The first end portion of the wick can be in fluid communication with the annular liquid storage tank via a first liquid lumen that extends through the first wall of the heater enclosure.

In accordance with one aspect of the present invention there is provided a battery connector for an electronic smoking device, comprising a base connector that includes a first horizontal cylindrical segment that extends along a longitudinal axis and defines a first flattened circumferential surface. A connection pad can be disposed on the first flattened circumferential surface and can include a connection lead. A press-fit-connector can comprise a second horizontal cylindrical segment that defines a second flattened circumferential surface. The press-fit-connector can be connected to the base connector such that the second flattened circumferential surface is opposed to the first flattened circumferential surface. The connection pad can be disposed between the first flattened circumferential surface and the second flattened circumferential surface.

In accordance with one aspect of the present invention there is provided an electronic smoking device, comprising an outer tube mounted around at least a portion of an inner tube. The outer tube can comprise an outer surface and an inner surface. The inner tube can comprise an inner surface defining an air path and an outer surface. An annular liquid storage tank can be defined between the outer surface of the inner tube and the inner surface of the outer tube. A mouth piece can be connected to a proximal end of the inner tube and to the outer tube. A heater enclosure can define a heater coil chamber. A distal end of the heater enclosure can define a chamber air inlet. A one way valve can be in fluid communication with the heater coil chamber via the chamber air inlet. The one way valve can be configured to allow airflow into the heater coil chamber from the air inlet. A heater coil can be mounted at least partially within the heater enclosure. A wick can include a first end portion and a second end portion. The wick can extend through a center of the heater coil, the first and second end portions being in fluid communication with the annular liquid storage tank. The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, the same element numbers indicate the same elements in each of the views:

FIG. 5B is an isometric side and top view of a base battery connector portion of an exemplary e-cigarette with memory;

FIG. 5C is an isometric side and bottom view of a press-fit-connector of an exemplary e-cigarette;

DESCRIPTION OF THE PREFERRED EMBODIMENTS

Figure 1:
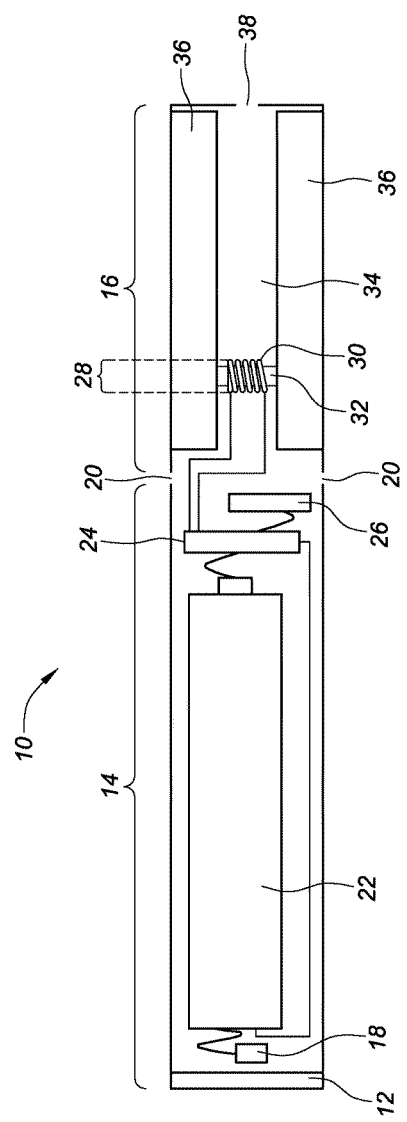
FIG. 1 is a schematic cross-sectional illustration of an exemplary e-cigarette.

Throughout the following, an electronic smoking device will be exemplarily described with reference to an e-cigarette. As is shown in FIG. 1, an e-cigarette 10 (also referred to herein as electronic smoking device) typically has a housing comprising a cylindrical hollow tube having an end cap 12. The cylindrical hollow tube may be a single-piece or a multiple-piece tube. In FIG. 1, the cylindrical hollow tube is shown as a two-piece structure having a power supply portion 14 and an atomizer/liquid reservoir portion 16 (also referred to herein as cartomizer). Together the power supply portion 14 and the atomizer/liquid reservoir portion 16 form a cylindrical tube which can be approximately the same size and shape as a conventional cigarette, typically about 100 mm with a 7.5 mm diameter, although lengths may range from 70 to 150 or 180 mm, and diameters from 5 to 28 mm.

The power supply portion 14 and atomizer/liquid reservoir portion 16 are typically made of metal (e.g., steel or aluminum, or of hardwearing plastic) and act together with the end cap 12 to provide a housing to contain the components of the e-cigarette 10. The power supply portion 14 and the atomizer/liquid reservoir portion 16 may be configured to fit together by, for example, a friction push fit, a snap fit, a bayonet attachment, a magnetic fit, or screw threads. The end cap 12 is provided at the front end of the power supply portion 14. The end cap 12 may be made from translucent plastic or other translucent material to allow a light-emitting diode (LED) 18 positioned near the end cap to emit light through the end cap. Alternatively, the end cap may be made of metal or other materials that do not allow light to pass.

An air inlet may be provided in the end cap, at the edge of the inlet next to the cylindrical hollow tube, anywhere along the length of the cylindrical hollow tube, or at the connection of the power supply portion 14 and the atomizer/liquid reservoir portion 16. FIG. 1 shows a pair of air inlets 20 provided at the intersection between the power supply portion 14 and the atomizer/liquid reservoir portion 16.

A power supply, preferably a battery 22, the LED 18, control electronics 24 and, optionally, an airflow sensor 26 are provided within the cylindrical hollow tube power supply portion 14. The battery 22 is electrically connected to the control electronics 24, which are electrically connected to the LED 18 and the airflow sensor 26. In this example, the LED 18 is at the front end of the power supply portion 14, adjacent to the end cap 12; and the control electronics 24 and airflow sensor 26 are provided in the central cavity at the other end of the battery 22 adjacent the atomizer/liquid reservoir portion 16.

The airflow sensor 26 acts as a puff detector, detecting a user puffing or sucking on the atomizer/liquid reservoir portion 16 of the e-cigarette 10. The airflow sensor 26 can be any suitable sensor for detecting changes in airflow or air pressure, such as a microphone switch including a deformable membrane which is caused to move by variations in air pressure. Alternatively, the sensor may be, for example, a Hall element or an electro-mechanical sensor.

The control electronics 24 are also connected to an atomizer 28. In the example shown, the atomizer 28 includes a heating coil 30 which is wrapped around a wick 32 extending across a central passage 34 of the atomizer/liquid reservoir portion 16. The central passage 34 may, for example, be defined by one or more walls of the liquid reservoir and/or one or more walls of the atomizer/liquid reservoir portion 16 of the e-cigarette 10. The coil 30 may be positioned anywhere in the atomizer 28 and may be transverse or parallel to a longitudinal axis of a cylindrical liquid reservoir 36. The wick 32 and heating coil 30 do not completely block the central passage 34. Rather an air gap is provided on either side of the heating coil 30 enabling air to flow past the heating coil 30 and the wick 32. The atomizer may alternatively use other forms of heating elements, such as ceramic heaters, or fiber or mesh material heaters. Nonresistance heating elements such as sonic, piezo, and jet spray may also be used in the atomizer in place of the heating coil.

The central passage 34 is surrounded by the cylindrical liquid reservoir 36 with the ends of the wick 32 abutting or extending into the liquid reservoir 36. The wick 32 may be a porous material such as a bundle of fiberglass fibers or cotton or bamboo yarn, with liquid in the liquid reservoir 36 drawn by capillary action from the ends of the wick 32 towards the central portion of the wick 32 encircled by the heating coil 30.

The liquid reservoir 36 may alternatively include wadding (not shown in FIG. 1) soaked in liquid which encircles the central passage 34 with the ends of the wick 32 abutting the wadding. In other embodiments, the liquid reservoir may comprise a toroidal cavity arranged to be filled with liquid and with the ends of the wick 32 extending into the toroidal cavity.

An air inhalation port 38 is provided at the back end of the atomizer/liquid reservoir portion 16 remote from the end cap 12. The inhalation port 38 may be formed from the cylindrical hollow tube atomizer/liquid reservoir portion 16 or may be formed in an end cap.

In use, a user sucks on the e-cigarette 10. This causes air to be drawn into the e-cigarette 10 via one or more air inlets, such as air inlets 20, and to be drawn through the central passage 34 towards the air inhalation port 38. The change in air pressure which arises is detected by the airflow sensor 26, which generates an electrical signal that is passed to the control electronics 24. In response to the signal, the control electronics 24 activate the heating coil 30, which causes liquid present in the wick 32 to be vaporized creating an aerosol (which may comprise gaseous and liquid components) within the central passage 34. As the user continues to suck on the e-cigarette 10, this aerosol is drawn through the central passage 34 and inhaled by the user. At the same time, the control electronics 24 also activate the LED 18 causing the LED 18 to light up, which is visible via the translucent end cap 12. Activation of the LED may mimic the appearance of a glowing ember at the end of a conventional cigarette. As liquid present in the wick 32 is converted into an aerosol, more liquid is drawn into the wick 32 from the liquid reservoir 36 by capillary action and thus is available to be converted into an aerosol through subsequent activation of the heating coil 30.

Some e-cigarette are intended to be disposable and the electric power in the battery 22 is intended to be sufficient to vaporize the liquid contained within the liquid reservoir 36, after which the e-cigarette 10 is thrown away. In other embodiments, the battery 22 is rechargeable and the liquid reservoir 36 is refillable. In the cases where the liquid reservoir 36 is a toroidal cavity, this may be achieved by refilling the liquid reservoir 36 via a refill port (not shown in FIG. 1). In other embodiments, the atomizer/liquid reservoir portion 16 of the e-cigarette 10 is detachable from the power supply portion 14 and a new atomizer/liquid reservoir portion 16 can be fitted with a new liquid reservoir 36 thereby replenishing the supply of liquid. In some cases, replacing the liquid reservoir 36 may involve replacement of the heating coil 30 and the wick 32 along with the replacement of the liquid reservoir 36. A replaceable unit comprising the atomizer 28 and the liquid reservoir 36 may be referred to as a cartomizer.

The new liquid reservoir may be in the form of a cartridge (not shown in FIG. 1) defining a passage (or multiple passages) through which a user inhales aerosol. In other embodiments, the aerosol may flow around the exterior of the cartridge to the air inhalation port 38.

Of course, in addition to the above description of the structure and function of a typical e-cigarette 10, variations also exist. For example, the LED 18 may be omitted. The airflow sensor 26 may be placed, for example, adjacent to the end cap 12 rather than in the middle of the e-cigarette. The airflow sensor 26 may be replaced by, or supplemented with, a switch which enables a user to activate the e-cigarette manually rather than in response to the detection of a change in airflow or air pressure.

Different types of atomizers may be used. Thus, for example, the atomizer may have a heating coil in a cavity in the interior of a porous body soaked in liquid. In this design, aerosol is generated by evaporating the liquid within the porous body either by activation of the coil heating the porous body or alternatively by the heated air passing over or through the porous body. Alternatively the atomizer may use a piezoelectric atomizer to create an aerosol either in combination or in the absence of a heater.

Figure 2A:
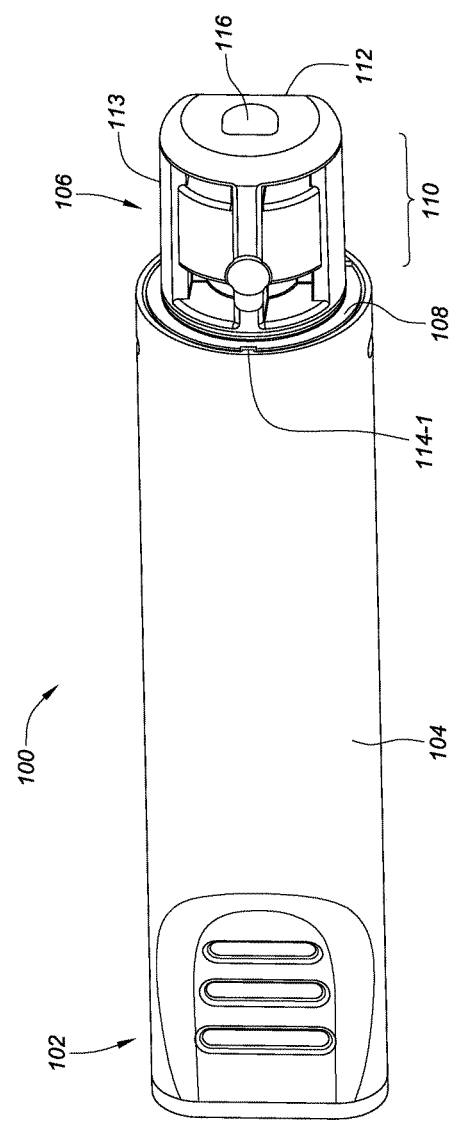
FIG. 2A is an isometric side, bottom, and distal end view of a cartomizer of an exemplary e-cigarette.

FIG. 2A is an isometric side, bottom, and distal end view of a cartomizer 100 of an exemplary e-cigarette. In an example, the cartomizer 100 can be connected with a power supply portion (e.g., battery) to provide power for an atomizer contained within the cartomizer 100. The cartomizer 100 can include a mouth piece portion 102 with one or more outlets (not shown), which can be configured for delivery of a vapor to a user.

The cartomizer 100 can include an outer tube 104 that is connected with the mouth piece portion 102. In an example, the mouth piece portion 102 can be connected with the outer tube 104 by press-fitting the mouth piece portion 102 into the outer tube 104 and/or through use of an adhesive applied between the outer tube 104 and the mouth piece portion 102, although other connecting technologies may be used. In some embodiments, the mouth piece portion 102, as well as other components of the cartomizer 100, can be connected with the outer tube 104 via a snap connecter, for example. In some embodiments, the mouth piece portion 102 and the outer tube 104 can be formed from a unitary piece of material.

The cartomizer 100 can include a battery connector 106 (e.g., a frictionally-engaged connector or other type of connector) that is configured to connect with (e.g., can be inserted into) a complementary connector comprising part of or associated with a housing for a power supply that is capable of providing power to an atomizer comprising part of the cartomizer 100; processing resources capable of executing instructions stored on a memory associated with the cartomizer 100; and/or memory. In an example, the battery connector 106 can be connected with the outer tube 104 by press-fitting the battery connector 106 into the outer tube 104. The battery connector 106 can include a tube mounting portion 108, a contact portion 110, and a coupling portion 111 (shown in FIG. 2B).

In some embodiments, the tube mounting portion 108 can have a diameter that is greater than, the same, or less than an inner diameter of the outer tube 104 and can be inserted into a distal end of the outer tube 104. The tube mounting portion 108 can include one or more alignment features 114-1 (114-2 is depicted in FIG. 2F), in some embodiments, that extend along a longitudinal portion of the tube mounting portion 108. In some embodiments, first and second alignment features 114-1, 114-2 can include a longitudinally extending groove and/or tongue that extends along the longitudinal portion of the tube mounting portion 108. In some embodiments, the inner surface of the outer tube 104 can include a complementary alignment feature. For example, where the tube mounting portion 108 includes a groove, the inner surface of the outer tube 104 can include a tongue that is configured to fit into the groove. In some embodiments, the battery connector 106 can define an air inlet 116, which comprises an axial cylindrical opening, which can pass through the battery connector 106 along a longitudinal axis of the battery connector 106.

Figure 2B:
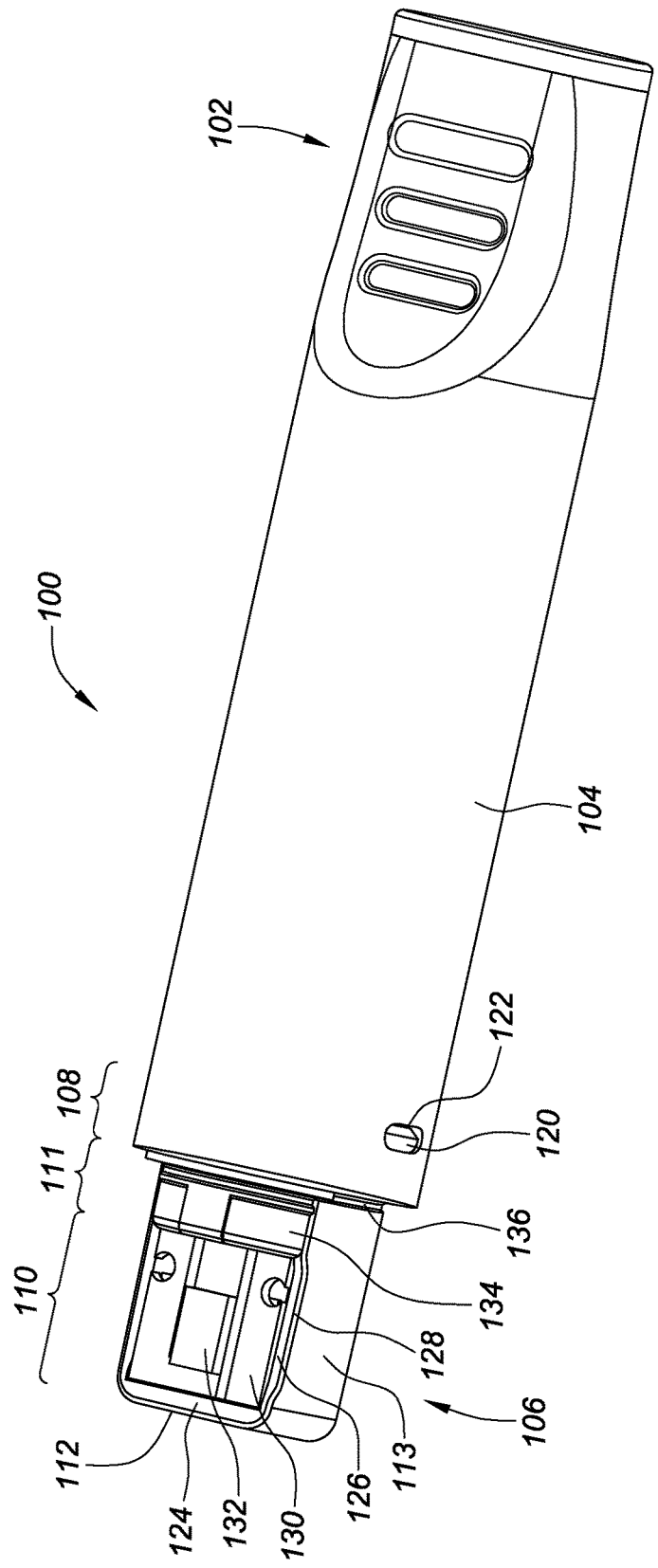
FIG. 2B is an isometric side and top view of the cartomizer depicted in FIG. 2A.

FIG. 2B is an isometric side and top view of the cartomizer depicted in FIG. 2A. The battery connector 106 can include a base connector 113 and a press-fit connector portion 134. The base connector 113 can be a horizontal cylindrical segment, which in some embodiments can be hemi-cylindrical in shape. The base connector 113 can include a contact portion 110 on a distal end of the base connector 113. The contact portion 110 can be a horizontal cylindrical segment, which in some embodiments can be hemi-cylindrical. The contact portion 110 can have an alignment feature 112, which can ensure that the contact portion 110 of the battery connector 106 is inserted with a correct orientation into the complementary connector that comprises the part of the housing for the power supply. The alignment feature 112 can include a flattened circumferential surface 124 of the horizontal cylindrical segment, which forms contact portion 110, in some embodiments. The flattened circumferential surface 124 can provide a mounting location for power, data connections and/or a memory, in some embodiments, as discussed further herein.

In some embodiments, the tube mounting portion 108 and the outer tube 104 can include complementary connectors. In an example, the tube mounting portion 108 can include a radially extending projection 120. In some embodiments, the radially extending projection 120 can be cylindrical and can extend from an outer surface of the tube mounting portion 108 transverse to a longitudinal axis of the battery connector 106. In some embodiments, the radially extending projection 120 can have a cross-section defined parallel to the longitudinal axis of the battery connector 106 that is circular, an ellipse, square, rectangular, etc.

The outer tube 104 can define a complementary connecter lumen 122 into which the radially extending projection can be inserted. For example, the outer tube 104 can define a hole formed with a shape that is complementary to the radially extending projection 120. For instance, the hole can extend through a wall of the outer tube 104 and can have a shape that is circular, an ellipse, square, rectangular, etc. In some embodiments, as previously discussed, the tube mounting portion 108 can have a diameter that is greater than, equal to, or less than an inner diameter of the distal end of the outer tube 104. In some embodiments where the tube mounting portion 108 has a diameter that is greater than the inner diameter of the distal end of the outer tube 104, upon insertion of the tube mounting portion 108 into the distal end of the outer tube 104, the distal end of the outer tube 104 can expand to accommodate the larger diameter tube mounting portion 108. This can provide for a secure fit between the battery connector 106 and the outer tube 104.

In some embodiments, the radially extending projection 120 can extend from the outer surface of the tube mounting portion 108. As the tube mounting portion 108 is inserted into the outer tube 104, the tube mounting portion 108 located adjacent to the radially extending projection 120 can deflect inward toward the longitudinal axis of the battery connector 106; and/or a portion of the outer tube 104 located adjacent to the complementary connector lumen 122 can deflect outward with respect to a longitudinal axis of the outer tube 104. When the radially extending projection 120 has been aligned with the complementary connector lumen 122, the tube mounting portion 108 and/or the outer tube 104 can deflect back to a natural state, causing the radially extending projection 120 to be disposed in the complementary connector lumen 122.

In some embodiments, a proximal face of the radially extending projection 120 can be angled and/or radiused to prevent interference between the proximal face of the radially extending projection 120 and a distal face of the outer tube 104. In some embodiments, a distal face of the radially extending projection 120 can be transverse to the longitudinal axis of the battery connector 106 to cause an interference fit between the distal face of the radially extending projection 120 and a distal side of the complementary connector 122; thus preventing the battery connector 106 from being pulled apart from the outer tube 104.

As previously discussed, the battery connector 106 can include an alignment feature 112. The alignment feature 112 can include a flattened circumferential surface 124, which can be planar and parallel to a longitudinal axis of the battery connector 106. As further discussed herein, a cross-sectional profile of the contact portion 110 transverse to a longitudinal axis of the battery connector 106 can be D-shaped. In some embodiments, the flattened circumferential surface 124 can include a circuit depression 126, formed in an outer surface of the flattened circumferential surface 124. In some embodiments, the circuit depression 126 can be defined by a lip 128 extending around a portion of a perimeter of the flattened circumferential surface 124, which is further discussed herein.

The contact portion 110 can include a connection pad 130, which can be connected to the contact portion 110. The connection pad 130 can be disposed in the circuit depression 126 of the flattened circumferential surface 124. The connection pad 130 can include an electrical connection, which can serve to provide power to an atomizer and/or other features included in the cartomizer 100 that may require power to operate, and a data connection, which can serve to provide a communication link with various features of the cartomizer. In some embodiments, a memory 132 (e.g., physical memory) can be in communication with the data connection portion of the connection pad 130. The memory 132 can store parameters associated with the atomizer, in some embodiments.

In some embodiments, the battery connector 106 can include a press-fit connector 134. The press-fit connector 134 can include a complementary surface to the flattened circumferential surface 124 of the base connector 113. In an example, the press-fit connector 134 can be a horizontal cylindrical segment that can include a flattened circumferential surface, which can be complementary to the flattened circumferential surface of the base connector 113 (e.g., both surfaces can be planar). In some embodiments, the press-fit connector 134 can be connected with the base connector 113, such that the flattened circumferential surfaces of the base connector 113 and the press-fit connector 134 can be opposed to one another. The base connector 113 and the press-fit connector 134 can together form the coupling portion 111 and the tube mounting portion 108.

In some embodiments, the base connector 113 and the press-fit connector 134 can define a circumferential groove 136 around the coupling portion 111. In some embodiments, the complementary connector comprising part of or associated with a housing for a power supply 14 can include a circumferential ridge that radially extends from an inner surface of complementary connector and is configured to fit into the circumferential groove 136. In some embodiments, the circumferential ridge and the coupling portion 111 can fit together to provide a frictional fit between the housing for the power supply 14 and the coupling portion 111.

Figure 2C:
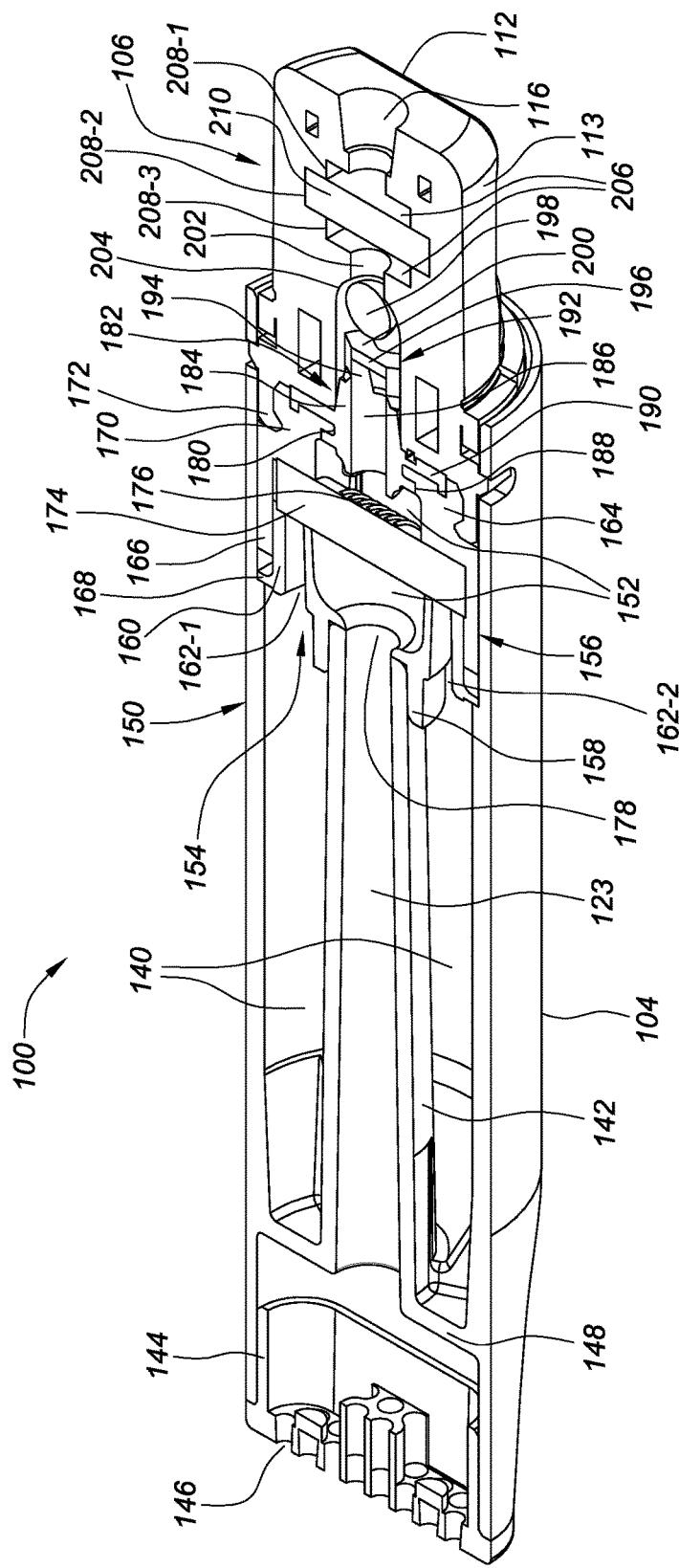
FIG. 2C is an isometric cross-sectional side, bottom, and distal end view of the cartomizer depicted in FIG. 2A.

FIG. 2C is an isometric cross-sectional side, bottom, and distal end view of the cartomizer depicted in FIG. 2A. The cartomizer 100 can include an annular liquid storage tank 140 that can be configured to hold liquid. In an example, the liquid can be vaporized by an atomizer and inhaled by a user. The liquid can include a flavoring and/or nicotine to enhance a user's experience. The annular liquid storage tank 140 can be annular in shape and can be defined by an outer surface of an inner tube 142 and an inner surface of an outer tube 104, which can be mounted around at least a portion of the inner tube 142. In some embodiments, the inner tube 142 and/or the outer tube 104 can be annular in shape. The inner tube 142 and the outer tube 104 can be connected with a mouth piece 144, in some embodiments. As such, vapor can travel through an air path 123 defined by an inner surface of the inner tube 142 and through a mouth piece passageway 146 formed in the mouth piece 144. In addition, by connecting the outer tube 104 to the mouth piece 144, a proximal end of the annular liquid storage tank 140 can be sealed by a connection between the outer tube 104 and the mouth piece 144 and a connection between the inner tube 142 and the mouth piece 144 and/or a proximal seal 148.

As depicted, in some embodiments, the proximal seal 148 can be placed between the inner tube 142 and the mouth piece 144, as illustrated in FIG. 2. For instance, the proximal seal 148 can radially extend from a proximal end of the inner tube 142. In an example, the proximal seal 148 can have an outer surface that connects with an inner surface of the outer tube 104 and can have an inner surface that connects with an outer surface of the inner tube 142, thus sealing the proximal end of the annular liquid storage tank 140.

In some embodiments, a distal end of the inner tube 142 can be connected with a heater coil enclosure 150 (e.g. heater enclosure), which defines a heater coil chamber 152. The heater coil enclosure 150 can be formed from a heater coil housing 154 and a heater coil support 156. The heater coil housing 154 can include a proximally extending housing neck portion 158 of a first diameter and a distally extending housing base portion 160 of a second diameter, which is greater than the first diameter. The housing neck portion 158 can have an inner diameter that is less than an inner diameter of the base portion, which forms a proximal portion of the heater coil chamber 152.

In some embodiments, the distal end of the inner tube 142 can be connected to the housing neck portion 158 of the heater coil housing 154. As depicted, an outer circumferential surface of the distal end of the inner tube 142 can be connected with an inner circumferential surface of the housing neck portion 158. However, although not depicted, in some embodiments, the outer circumferential surface of the housing neck portion 158 can be connected with an inner circumferential surface of the inner tube 142. In some embodiments, an interface between the distal end of the inner tube 142 and the heater coil housing 154 can form a chamber air outlet 178.

The housing base portion 160 can include a flared proximal lip 168, in some embodiments. An outer circumference of flared proximal lip 168 can be connected with an inner wall of the outer tube 104, in some embodiments, which can form a seal between the inner wall of the outer tube 104 and the outer circumferential surface of the flared proximal lip 168, thus preventing liquid from leaking out of the annular liquid storage tank 140.

The heater coil support 156 can be annular in shape and can include a support neck portion 164 and a support base portion 166. In some embodiments, an inner diameter of the support base portion 166 of the heater coil support 156 can be greater than an outer diameter of the housing base portion 160 of the heater coil housing 154. The support base portion 166 of the heater coil support 156 can be disposed around the housing base portion 160 of the heater coil housing 154 and connected with the housing base portion 160 of the heater coil housing 154. The heater coil housing 154 and the heater coil support 156 define the heater coil chamber 152 between the housing neck portion 158 of the heater coil housing 154 and a distal end of the support neck portion 164 of the heater coil support 156.

In some embodiments, a distal end of the heater coil support 156 can be connected to the proximal end of the battery connector 106. In an example, a distal outer circumferential surface of the support neck portion 164 can define a circumferential support groove 170. The circumferential support groove 170 can circumferentially extend around a portion of an outer surface of the support neck portion 164. The proximal end of the battery connector 106 can include a circumferential ridge 172 that circumferentially extends around an inner surface of the proximal end of the battery connector 106. In some embodiments, the battery connector 106 and the heater coil support 156 can be formed of a semi-rigid material, which can allow an inner diameter of the circumferential ridge 172 to expand and contract as the battery connector 106 and the heater coil support 156 are pushed together. In an assembled state, the circumferential ridge 172 can be disposed in the circumferential support groove 170.

In some embodiments, the heater coil enclosure 150 can house a wick 174. Either end of the wick 174 can be captured via complementary wick notches that form ports in the heater coil housing 154 and the heater coil support 156 (further depicted and described herein). The wick 174 can extend through a center of a heater coil 176, which in some embodiments can be circumferentially wrapped around the wick 174 and can be at least partially mounted within the heater coil enclosure 150.

In some embodiments, the heater coil housing 154 can define a first liquid lumen 162-1 and a second liquid lumen 162-2, configured to provide liquid from the annular liquid storage tank 140 to the wick 174. The first liquid lumen 162-1 can longitudinally extend through a first side of the heater coil housing 154 and the second liquid lumen 162-2 can longitudinally extend through a second side of the heater coil housing 154, diametrically opposed to the first liquid lumen 162-1. In some embodiments, the first liquid lumen 162-1 and the second liquid lumen 162-2 can be defined by the heater coil housing 154, such that the first liquid lumen 162-1 and the second liquid lumen 162-2 can pass through the heater coil housing 154 parallel to a longitudinal axis of the heater coil housing 154. The first liquid lumen 162-1 and the second liquid lumen 162-2 can provide liquid passageways from the annular liquid storage tank 140 to each end of the wick 174. For example, each liquid lumen 162-1, 162-2 can provide liquid to each end of the wick 174. Thus, liquid can absorb into the wick 174 from either end of the wick 174 and can be atomized by the heater coil 176.

In some embodiments, the distal end of the support neck portion 164 of the heater coil support 156 can define an inlet lumen 180. As depicted, the inlet lumen 180 can be circular. However, the distal end of the support neck portion 164 can define the inlet lumen 180 as other shapes, such as a square, triangle, oval, etc. In some embodiments, a valve grommet 182 can include an elongate body 184 that extends along a longitudinal axis. The elongate body 184 can define a lumen, which is referred to herein as a chamber air inlet 186. The proximal end of the elongate body 184 can include a proximal flange 188 and a distal flange 190.

The proximal flange 188 and the distal flange 190 can extend outwardly from the elongate body 184 and in some embodiments transverse to a longitudinal axis of the elongate body 184. The distal flange 190 can extend outwardly from the elongate body 184 and in some embodiments transverse to a longitudinal axis of the elongate body 184. In some embodiments, a diameter of the proximal flange 188 can be less than a diameter of the distal flange 190, which can allow for the proximal flange 188 to be pushed through the inlet lumen 180. For example, the valve grommet 182 can be formed from a flexible material (e.g., rubber) to allow for the proximal flange 188 to flex and be pushed through the inlet lumen 180.

In some embodiments, the distal end of the valve grommet 182 can include an airflow admitter 192. The airflow admitter 192 can be configured to allow for unrestricted airflow into the heater coil chamber 152 via the chamber air inlet 186. The airflow admitter 192 can work in combination with a valve ball 198, valve chamber 200, and a valve opening 202 defined by the base connector 113 to allow for airflow to enter the heater coil chamber 152 but restrict an airflow out of the valve opening 202. For example, air can flow one way with respect to the cartomizer 100. While air can flow into the cartomizer 100, air or a minimal amount of air is allowed to flow out of the cartomizer 100.

In an example, the valve chamber 200 can be defined by walls of the base connector 113 and can have a diameter that is greater than a diameter of the valve ball 198 to allow an airflow to pass around the valve ball 198 in the valve chamber 200. In some embodiments, the valve ball 198 can be formed from metal and/or plastic. This can allow the valve ball 198 to move longitudinally in the valve chamber 200. The valve opening 202 can be defined by the base connector 113 and can be disposed at a distal end of the valve chamber 200. The valve opening 202 can have a smaller diameter than the valve chamber 200 and a smaller diameter than the valve ball 198.

As a user draws air through the mouth piece 144, air can enter through the valve opening 202 and can travel proximally through the valve chamber 200. As the airflow enters through the valve opening 202, the airflow can move the valve ball 198 from the valve opening 202. For example, the airflow can flow around the valve ball 198 and lift the valve ball 198 from the valve opening 202, thus allowing air to enter into the valve chamber 200. In some embodiments, airflow admitter 192 can function to block the valve ball 198 from entering the chamber air inlet 186. For example, the airflow admitter 192 forms a cage over an entrance of the chamber air inlet 186, thus preventing the valve ball 198 from entering the chamber air inlet 186 and/or blocking an entrance of the chamber air inlet 186 (e.g., preventing an airflow from passing through the chamber air inlet 186).

In some embodiments, the airflow admitter 192 can comprise one or more longitudinally extending arms (e.g., longitudinally extending arm 194) that encircle a distal opening of the chamber air inlet 186. For example, the one or more longitudinally extending arms can be disposed on a distal end of the valve grommet 182 about the chamber air inlet 186. Although the cross-sectional view depicted in FIG. 2C depicts two longitudinally extending arms 194, the airflow admitter 192 can include more than or less than two longitudinally extending arms 194. For example, as further discussed herein, the airflow admitter 192 can include three longitudinally extending arms 194. In some embodiments, the distal ends of the longitudinally extending arms 194 can be connected via an arm connector 196. The arm connector 196 can connect each one of the longitudinally extending arms 194 together, in some embodiments.

In some embodiments, the walls of the base connector 113 that define the valve chamber 200 can be radiused toward the valve opening 202 at a distal end of the valve chamber 200 to form a radiused wall 204 that circumferentially extends around the proximal side of the valve opening 202. The radiused wall 204 can help to create a seal with the valve ball 198. Accordingly, as air flows into the valve chamber 200 from the chamber air inlet (e.g., as a result of a user blowing on the mouth piece 144), the valve ball 198 can be cradled by the radiused wall 204, creating a seal and preventing air from flowing through the valve opening 202.

In some embodiments, the base connector 113 can define an air inlet chamber 206. The air inlet chamber 206 can be defined by an inner wall of the base connector 113. In some embodiments, the air inlet chamber 206 can be a cylindrical chamber that extends along a longitudinal axis of the base connector 113. In some embodiments, the air inlet chamber 206 can be defined by the inner wall of the base connector 113, which comprises a first inner wall 208-1 with a first diameter, a second inner wall 208-2 with a second diameter, and a third inner wall 208-3 with a second diameter. As depicted, the first diameter can be less than the second diameter and equal to the third diameter. The second inner wall 208-2 with the second diameter can form a slot in which a porous material 210 (e.g., absorbent material) can be placed, as depicted in FIG. 2C.

The porous material 210 can be formed of an absorbent material, in some embodiments. The porous material 210 can prevent liquid from traveling from the portion of the air inlet chamber defined by the third inner wall 208-3 from leaking into the portion of the air inlet chamber defined by the first inner wall 208-1; and thus preventing liquid from leaking out of the air inlet 116, as further discussed herein. In some embodiments, the porous material 210 can include hydrophobic properties. In some embodiments, the porous material 210 can include oleophobic properties. For example, the porous material 210 can include a hydrophobic and/or oleophobic coating. In some embodiments, the properties of the porous material 210 can be configured to repel moisture created by a user's breath passing into the cartomizer from the mouth piece 144 and/or repel liquid that has dripped from the wick 174 and/or condensed from vapor in the heater coil chamber 152.

The base connector 113 can include an alignment feature 112, in some embodiments. The base connector 113 can define the air inlet 116, which can be defined by a cylindrical wall that extends through a distal face of the base connector 113, along a longitudinal axis of the base connector 113. In some embodiments, the air inlet 116 can be frustoconical. For example, a diameter of the air inlet 116 can decrease from a distal end of the air inlet 116, proximally along the length of the air inlet 116. This can cause a velocity of air passing through the air inlet 116 to be increased, thus providing a higher velocity airflow, which can improve atomization of the liquid.

In some embodiments, the cartomizer can be connected to the power supply portion 14 (FIG. 1), which can include control electronics, as well as an airflow sensor 26 (FIG. 1). The electronics and the airflow sensor 26 can be susceptible to moisture, in some embodiments. Accordingly, embodiments of the present disclosure can prevent moisture from contacting the control electronics, airflow sensor 26, and/or other components housed in the power supply portion 14. For example, one cause of moisture contacting the components in the power supply portion 14 can be a user blowing into the cartomizer 100 via the mouth piece 144. Blowing into the cartomizer 100 can cause moisture from a user's breath to condense in the cartomizer 100, potentially causing droplets of water to coalesce. Alternatively, or in addition, the user's breath can carry with it liquid that has dripped from the wick 174. This condensation and/or liquid from the wick 174 can travel distally down the cartomizer 100 along with the user's breath and could potentially exit air inlet 116 of the cartomizer 100, causing condensation/liquid to enter the power supply portion 14. Embodiments of the present disclosure can prevent this phenomenon from occurring. For example, as a user blows into the mouth piece 144, the valve ball 198 can be positioned over the valve opening 202, which can prevent air from traveling through the cartomizer 100 and out of the air inlet 116. As a result, moisture is also prevented from traveling through the cartomizer 100 and out of the air inlet 116. In addition, if the cartomizer is held vertically, gravity can cause the valve ball 198 to be positioned over the valve opening 202, preventing moisture from exiting the valve opening 202 and entering into the air inlet chamber 206. However, even if moisture from the liquid and/or user's breath enters the air inlet chamber 206, the porous material 210 can absorb and retain the moisture, preventing it from exiting the air inlet 116.

In some embodiments, the porous material 210 can comprise hydrophobic and/or oleophobic properties, which can cause moisture to be repelled from the porous material 210, preventing the moisture from traveling from a proximal side of the porous material 210 to a distal side of the porous material 210 and out of the air inlet 116. This can cause moisture to remain in portions of the cartomizer 100 that are located proximally with respect to the porous material 210 (e.g., the portion of the air inlet chamber 206 defined by the third inner wall 208-3). The airflow admitter 192, valve chamber 200, valve ball 198, and valve opening 202 can function as a one way valve. However, other types of one way valves can be utilized with various embodiments of the present disclosure. For example, a one way valve can be disposed in the inlet lumen 180 and/or distally with respect to the inlet lumen 180 to provide for a one way flow of air.

Accordingly, as a user sucks on the mouth piece 144, air can be drawn into the air inlet 116 and into a portion of the air inlet chamber 206 formed by the first inner wall 208-1. The air can be drawn across the porous material 210 and into the portion of the air inlet chamber formed by the third inner wall 208-3. The air can continue through the valve opening 202 and into the valve chamber 200. If the valve ball 198 was seated in the proximal side of the valve opening 202, the force of the airflow moving past the valve ball 198 can lift the valve ball 198 proximally from its seated position, allowing air to freely flow through the valve opening 202, into the valve chamber. As the valve ball 198 is lifted proximally from its seated position, the airflow admitter 192 of the valve grommet 182 can prevent the valve ball 198 from being lodged in an opening of the chamber air inlet 186. Thus, air can flow around the longitudinally extending arm(s) 194 and into the chamber air inlet 186 and into the heater coil chamber 152.

Air being drawn into the air inlet 116 as a result of the user sucking on the mouth piece 144 can cause air to be drawn across the airflow sensor, which can be housed in the power supply portion 14. A computer executable instruction can be executed by a processor in communication with the airflow sensor, causing the heater coil 176 to be activated. The air can flow across the wick 174 and heater coil 176, bringing with it vapor that has been generated by the atomization of liquid, which can be atomized via the heater coil 176 and wick 174. The vapor can be carried through the chamber air outlet 178 and into the air path 123 defined by the inner surface of the inner tube 142 and through a mouth piece passageway 146 formed in the mouth piece 144.

Figure 2D:
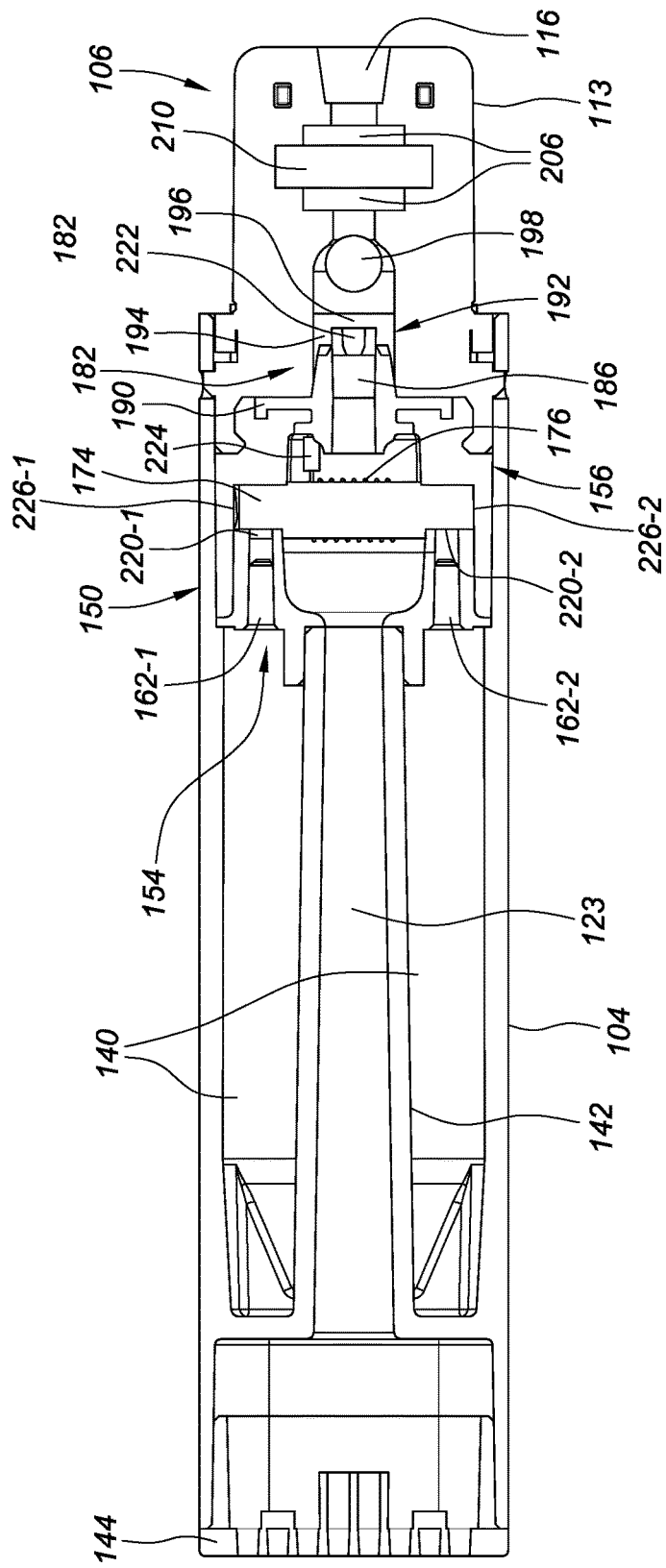
FIG. 2D is a cross-sectional view of the cartomizer depicted in FIG. 2A.

FIG. 2D is a cross-sectional view of the cartomizer depicted in FIG. 2A. As further depicted in FIG. 2D, the heater coil housing 154 defines the first liquid lumen 162-1 and the second liquid lumen 162-2. Liquid can flow from the annular liquid storage tank 140 and through the first and second liquid lumens 162-1, 162-2. The liquid can contact the wick 174 at respective first and second liquid/wick interfaces 220-1, 220-2 between the wick 174 and the first and second liquid lumens 162-1, 162-2.

In some embodiments, the wick 174 can include a first end portion and a second end portion and can extend through a center of the heater coil 176. The first end portion can extend into a first wick bore 226-1 defined in a first wall of the heater coil enclosure 150 and the second end portion can extend into a second wick bore 226-2 defined in a second wall of the heater coil enclosure 150. In some embodiments, the first end portion of the wick 174 can be in fluid communication with the annular liquid storage tank 140 via a first liquid lumen 162-1 that extends through the first wall of the heater coil enclosure 150; and the second end portion of the wick 174 can be in fluid communication with the annular liquid storage tank 140 via a second liquid lumen 162-2 that extends through the second wall of the heater coil enclosure 150.

As previously discussed, the valve grommet 182 can include an airflow admitter 192. The airflow admitter 192 can be formed by a longitudinally extending arm(s) 194. The longitudinally extending arm(s) 194 can be equally spaced about a distal end of the flow admitter and around the chamber air inlet 186. The longitudinally extending arm(s) 194 can be connected at their distal ends via an arm connector 196. As such, the longitudinally extending arm(s) 194 in combination with the arm connector 196 can define an airflow admitter aperture 222 through which air can flow. As previously discussed, the airflow admitter 192 can prevent the valve ball 198 from blocking an entrance of the chamber air inlet 186. Although the airflow admitter 192 is depicted as being formed as a separate component, the airflow admitter 192 can be integrally formed with the support neck portion 164 of the heater coil support 156. In some embodiments, a screen can be disposed over a portion of the air path located proximally with respect to the valve ball 198, preventing the valve ball 198 from blocking the air path. Alternatively, a pin can be inserted across the air path located proximally with respect to the valve ball 198 to prevent the valve ball 198 from blocking the air path.

In some embodiments, the distal flange 190 of the valve grommet 182 can create a seal between the heater coil support 156 and the base connector 113. The airflow sensor, in some embodiments can be included in the power supply portion 14. The heater coil 176 can be controlled, based on measurements taken by the airflow sensor. For example, power can be provided from the power supply portion 14 via a coil power lead 224, based on the measurements taken by the airflow sensor. As such, it can be important that the same amount of airflow that is measured by the airflow sensor disposed in the power supply portion 14 is delivered to the wick 174 and heater coil 176. Accordingly, the distal flange 190 can create a seal between the heater coil support 156 and the base connector 113, preventing air from escaping from the joint between the heater coil support 156 and the base connector 113 and preventing air from entering from the joint between the heater coil support 156 and the base connector 113.

Figure 2E:
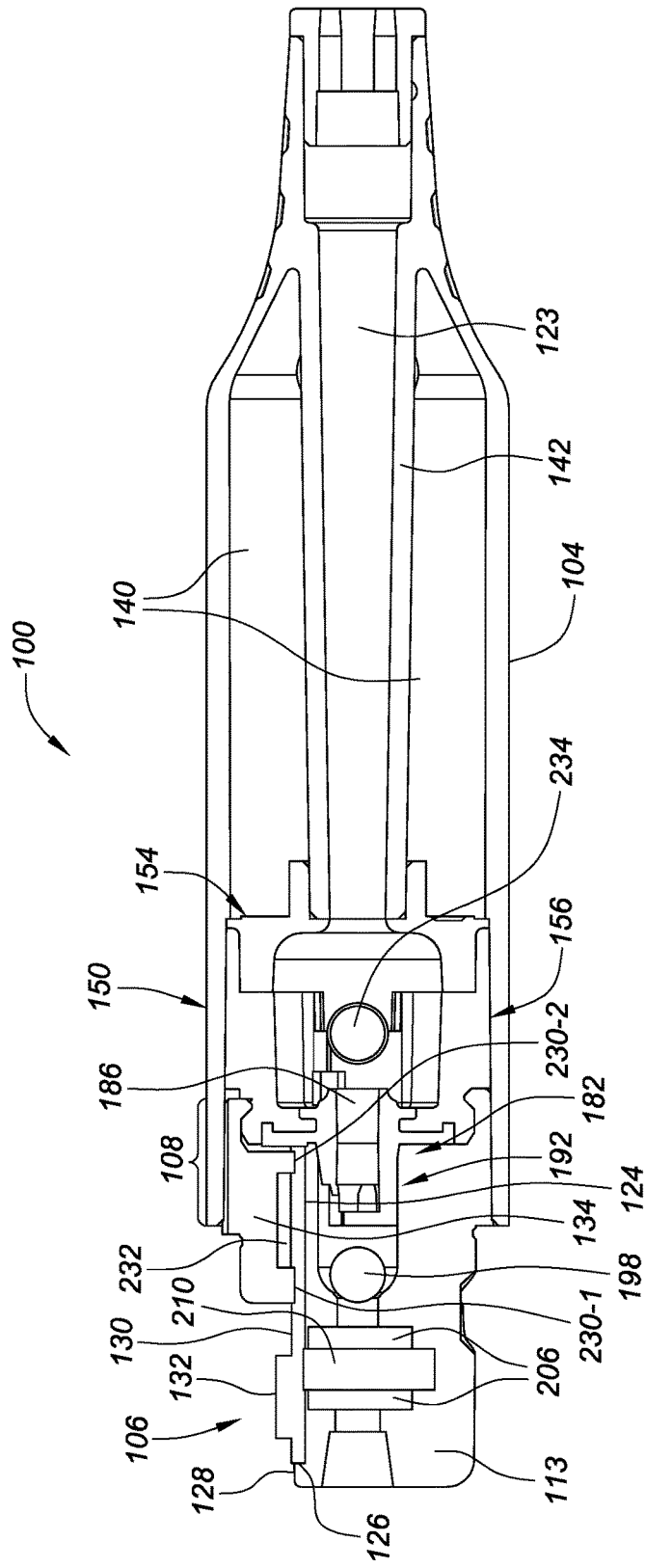
FIG. 2E is an isometric cross-sectional side view of the cartomizer depicted in FIG. 2A.
Figure 2F:
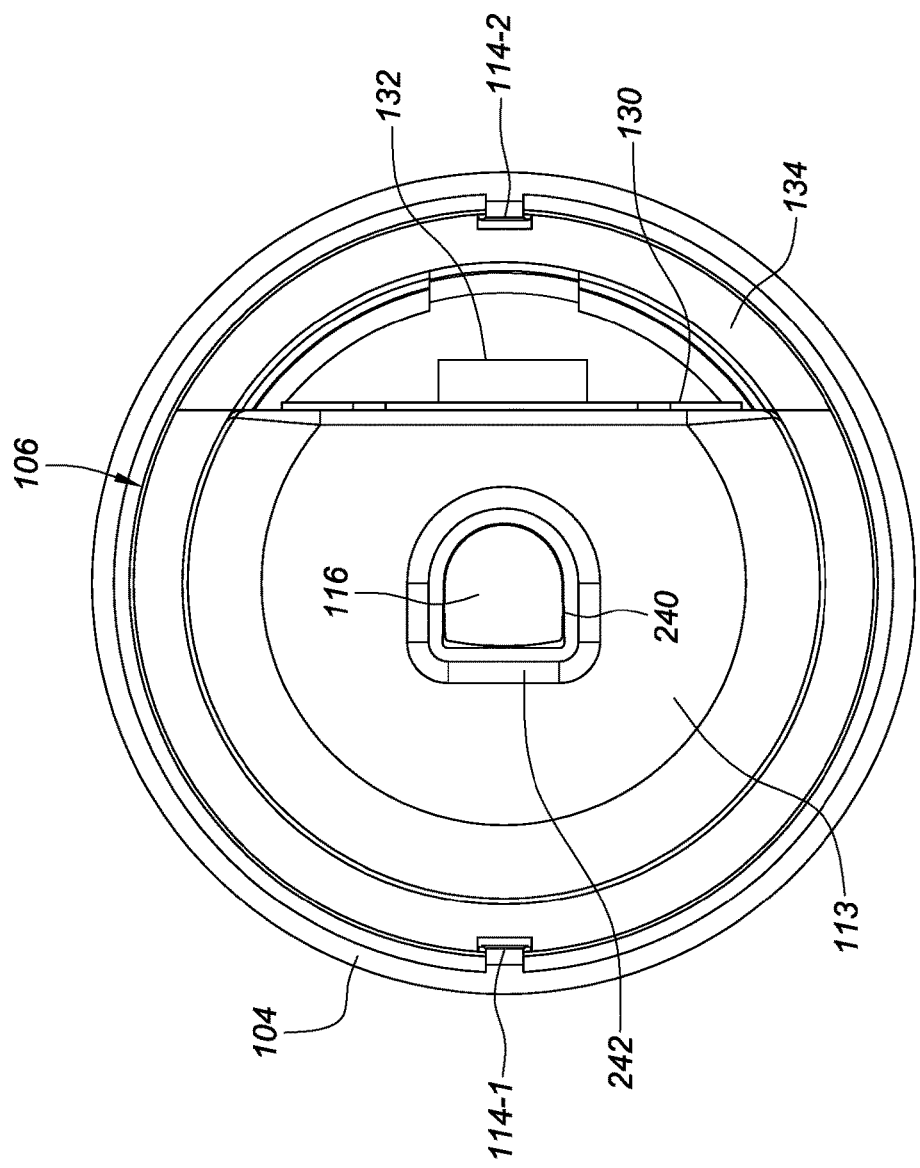
FIG. 2F is a distal end view of the cartomizer depicted in FIG. 2A.

FIG. 2E is an isometric cross-sectional side view of the cartomizer 100 depicted in FIG. 2A. The battery connector 106 of the cartomizer 100 can include a base connector 113 and a press-fit connector portion 134. The connection pad 130 can include an electrical connection and a data connection, as previously discussed. In some embodiments, the memory 132 can be connected to the connection pad 130. As previously discussed, the flattened circumferential surface 124 can include a circuit depression 126, that is defined by a lip 128, which can extend around a portion of a perimeter of the flattened circumferential surface 124. The circuit depression 126 can be sized to accept the connection pad 130. For example, the circuit depression 126 can have a length and width that is larger than the connection pad 130.

The press-fit connector 134 can include one or more flattened complementary surfaces 230-1, 230-2 that that can be complementary to the flattened circumferential surface 124 of the base connector 113. In an example, the press-fit connector 134 can be a horizontal cylindrical segment that can include first and second flattened circumferential surfaces 230-1, 230-2, which can be complementary to the flattened circumferential surface 124 of the base connector 113. In some embodiments, the press-fit connector 134 can be connected with the base connector 113, such that the flattened circumferential surface 124 of the base connector 113 and the complementary surfaces 230-1, 230-2 of the press-fit connector 134 can be opposed to one another. The base connector 113 and the press-fit connector 134 can together form the coupling portion 111 and the tube mounting portion 108, as depicted and discussed herein.

In some embodiments, the connection pad 130 can be sandwiched by the flattened circumferential surface 124 of the base connector 113 and the one or more complementary surfaces 230-1, 230-2 of the press-fit-connector 134. In some embodiments, the press-fit connector 134 can include a memory slot 232. Although the memory 132 is depicted as being disposed on a distal end of the connection pad 130, the memory 132 can be disposed in the memory slot 232 in some embodiments, as further discussed herein.

In some embodiments, the press-fit-connector 134 can be connected with the base connector 113 via connection tabs, as further discussed herein. Upon connection of the press-fit-connector 134 and the base connector 113 (e.g., thus sandwiching the connection pad 130, and in an embodiment, the memory 132 between the press-fit-connector 134 and the base connector 113) to form the battery connector 106, a longitudinal axis of the battery connector 106 can be aligned with the longitudinal axis of the cartomizer 100 and the battery connector 106 can be inserted into the distal end of the cartomizer 100. For example, the tube mounting portion 108 of the battery connector 106 can be inserted into the distal end of the cartomizer 100. In some embodiments, an inner diameter of the distal end of the outer tube 104 can be less than the outer diameter of the tube mounting portion 108. Accordingly, as the tube mounting portion 108 of the battery connector 106 is inserted into the distal end of the cartomizer 100, the press-fit-connector 134 and the base connector 113 can be pressed together. For example, the press-fit-connector 134 and the base connector 113 can both be pressed against the connection pad 130. In some embodiments where the memory is included in the memory slot 232, the memory can be pressed against the connection pad 130 via the press-fit-connector 134. In an example, the inner surface of the distal end of the outer tube 104 can press against the tube mounting portion 108, creating a radial force that is directed inwardly toward the longitudinal axis of the tube mounting portion 108.

In some embodiments, the air inlet chamber 206 can be a trench in the flattened circumferential surface 124. By forming the air inlet chamber 206 as a trench in the flattened circumferential surface 124, the porous material 210 can be placed in the air inlet chamber, prior to the connection pad 130 being positioned in the circuit depression 126.

FIG. 2F is a distal end view of the cartomizer depicted in FIG. 2A. As previously discussed, the battery connector 106 can be disposed in the distal end of the outer tube 104. To ensure a proper alignment of the battery connector 106 with the outer tube and/or a proper alignment between the press-fit-connector 134 and the base portion 113, the base portion 113 and/or the press-fit-connector 134 can include first and second alignment features 114-1, 114-2, which have corresponding features disposed in the inner wall of the outer tube 104. The connection pad 130 can be disposed on top of the flattened circumferential surface of the base connector 113, along with the memory 132. In some embodiments, the air inlet 116 can have a D-shape, which is defined by D-shaped walls 240 that extend through the base portion, along a longitudinal axis of the base connector 113. In some embodiments, a distal end of the walls can have a chamfered region 242, as depicted, which can be configured to accept an air inlet connector.

Figure 3A:
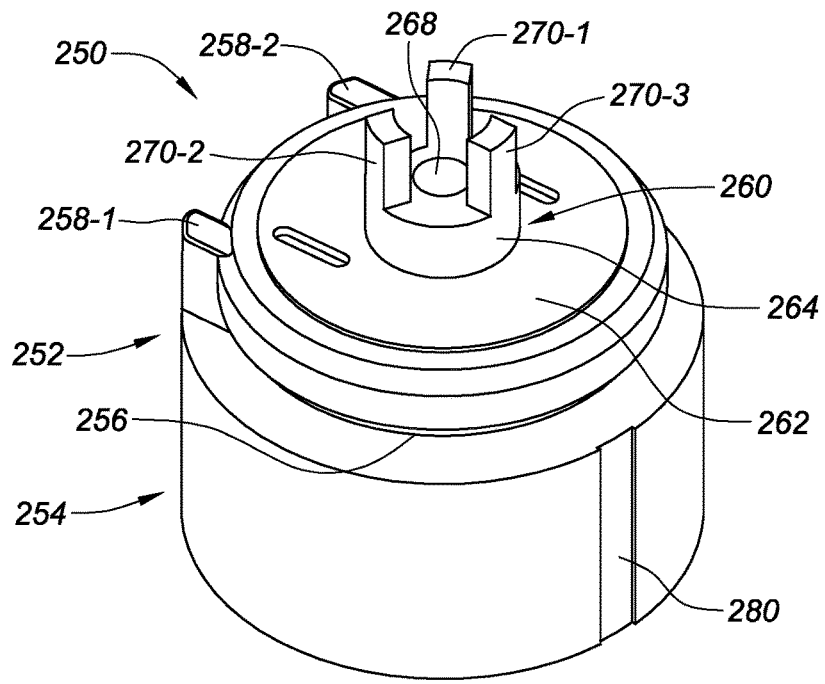
FIG. 3A is an isometric side and distal end view of a heater coil support of an exemplary e-cigarette.

FIG. 3A is an isometric side and distal end view of a heater coil support 250 of an exemplary e-cigarette. The heater coil support 250 can be annular in shape and can include a support neck portion 252 and a support base portion 254. In some embodiments, the support neck portion 252 can have a diameter that is less than a diameter of the support base portion 254. In some embodiments, the heater coil support 250 can include a support groove 256 disposed in an outer surface of the heater coil support 250, between the support neck portion 252 and the support base portion 254. The support groove 256 can circumferentially extend around the heater coil support 250, transverse to a longitudinal axis of the heater coil support 250. In some embodiments, the distal end of the support neck portion 252 can include one or more support alignment features 258-1, 258-2. For example, the distal end of the support neck portion 252 can include first and second support alignment features 258-1, 258-2, which can aid in alignment of the heater coil support 250 and a battery connector, as discussed herein. In some embodiments, the battery connector can include a complementary support alignment feature, as discussed in relation to FIG. 5B. An outer surface of the support base portion 254 can include one or more longitudinally extending grooves 280, which can act as alignment features, in some embodiments.

As depicted in FIG. 3A, the heater coil support 250 can include a valve grommet 260, as previously discussed herein. The valve grommet 260 can include a distal flange 262 and an elongate body 264. The distal flange 262 can extend outwardly from the elongate body 264 and transverse to a longitudinal axis of the elongate body 264. In some embodiments, the elongate body 264 can extend through an inlet lumen of the heater coil support 250 and can be held in place via a combination of the distal flange 262 and a proximal flange 266 (FIG. 3B), which can also extend outwardly from the elongate body 264 and transverse to a longitudinal axis of the elongate body 264. A distal face of the heater coil support 250 can be disposed between the proximal flange 266 and the distal flange 262. As previously discussed, a diameter of the distal flange 262 and the proximal flange 266 can be larger than a diameter of the inlet lumen of the heater coil support.

The elongate body 264 can define a chamber air inlet 268, which extends through a longitudinal length elongate body 264. In some embodiments, the distal end of the elongate body 264 can include one or more longitudinally extending arms 270-1, 270-2, 270-3 that encircle a distal opening of the chamber air inlet 268. Although first, second, and third longitudinally extending arms 270-1, 270-2, 270-3 are depicted, fewer than three or greater than three longitudinally extending arms 270-1, 270-2, 270-3 can encircle the distal opening of the chamber air inlet 268. The purpose of the longitudinally extending arms is to prevent the valve ball 198, as previously discussed, from blocking the chamber air inlet 268 (e.g., from becoming seated in the chamber air inlet 268). In some embodiments, a single longitudinally extending arm can extend from the distal opening of the chamber air inlet 268 to prevent the valve ball 198 from covering the chamber air inlet 268. In some embodiments, a longitudinal slot can be defined in a sidewall of the elongate body 264 that extends distally from the distal flange 262 to allow air to flow through the longitudinal slot. In some embodiments, the distal surface of the elongate body 264 can be formed as an uneven surface (e.g., can include bumps or protrusions) such that air can flow between the bumps and/or protrusions and valve ball 198 seated on top of the bumps and/or protrusions.

Figure 3B:
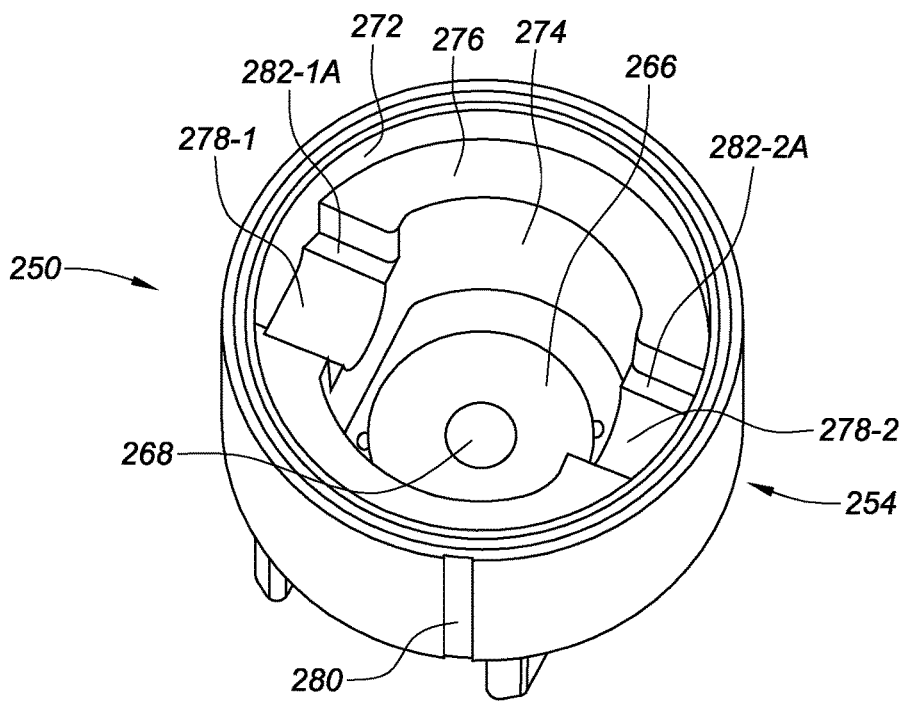
FIG. 3B is an isometric side and proximal end view of the heater coil support depicted in FIG. 3A.

FIG. 3B is an isometric side and proximal end view of the heater coil support 250 depicted in FIG. 3A. The heater coil support 250 can include the support neck portion 252. Heater coil support 250 can include a proximal neck portion 272 of a first diameter and a distal neck portion 274 of a second diameter, which is less than the first diameter of the proximal neck portion 272. This can form an inner annular ledge 276, which serves as a stop portion, preventing a heater coil housing from being inserted too far into the heater coil support 250. A first wick housing notch 278-1 and a second wick housing notch 278-2 can be defined in the annular ledge 276 of the support base portion 254. In some embodiments, the first wick housing notch 278-1 and the second wick housing notch 278-2 can be semi-circular, such that a wick can fit in the first wick housing notch 278-1 and the second wick housing notch 278-2. The heater coil housing (FIG. 4A to 4C) can include complementary wick support notches. In some embodiments, upon assembly of the heater coil housing and the heater coil support 250, the ports (e.g., port 234 in FIG. 2E) can be formed and the wick can be held in place between the heater coil housing and the heater coil support 250.

In some embodiments, the heater coil support 250 can include mount stop portions 282-1A, 282-2A, located between the annular ledge 276 and on either side of the heater coil notches 278-1, 278-2. Although only mount stop portions 282-1A, 282-2A are depicted, additional mount stop portions (282-1B, 282-2B) are included on the other side of the heater coil notches 278-1, 278-2 from the mount stop portions 282-1A, 282-2A. Distal ends of the wick mounts (e.g., wick mount 318-1) can contact the mount stop portions 282-1A, 282-2A, further discussed in relation to FIG. 4C.

Figure 4A:
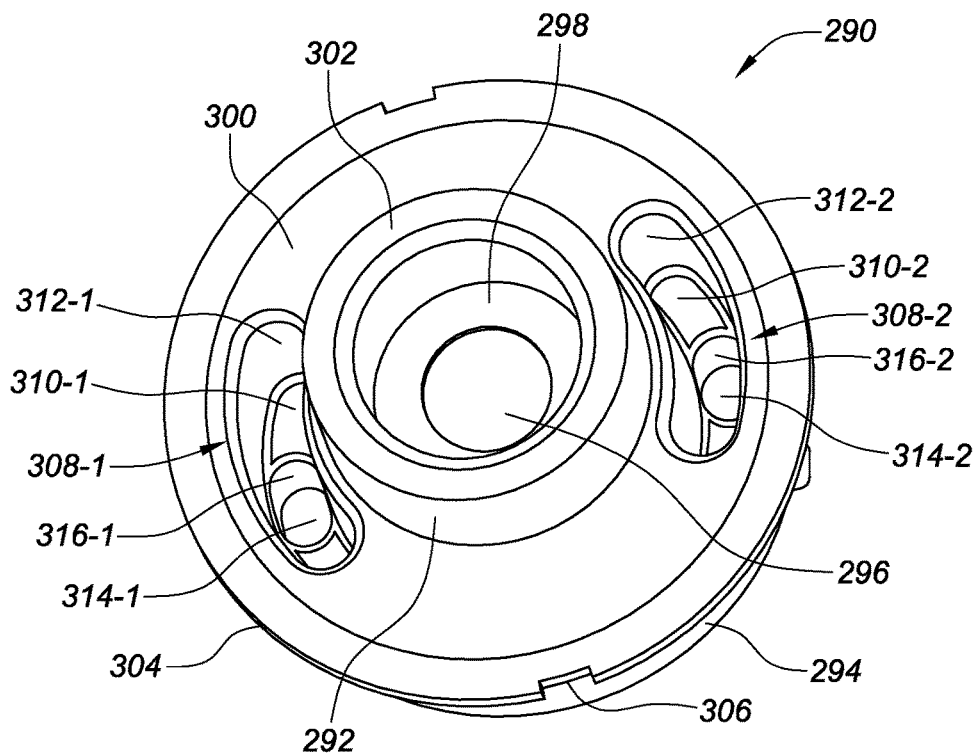
FIGS. 4A and 4B are isometric side and proximal end views of a heater coil housing of an exemplary e-cigarette.
Figure 4B:
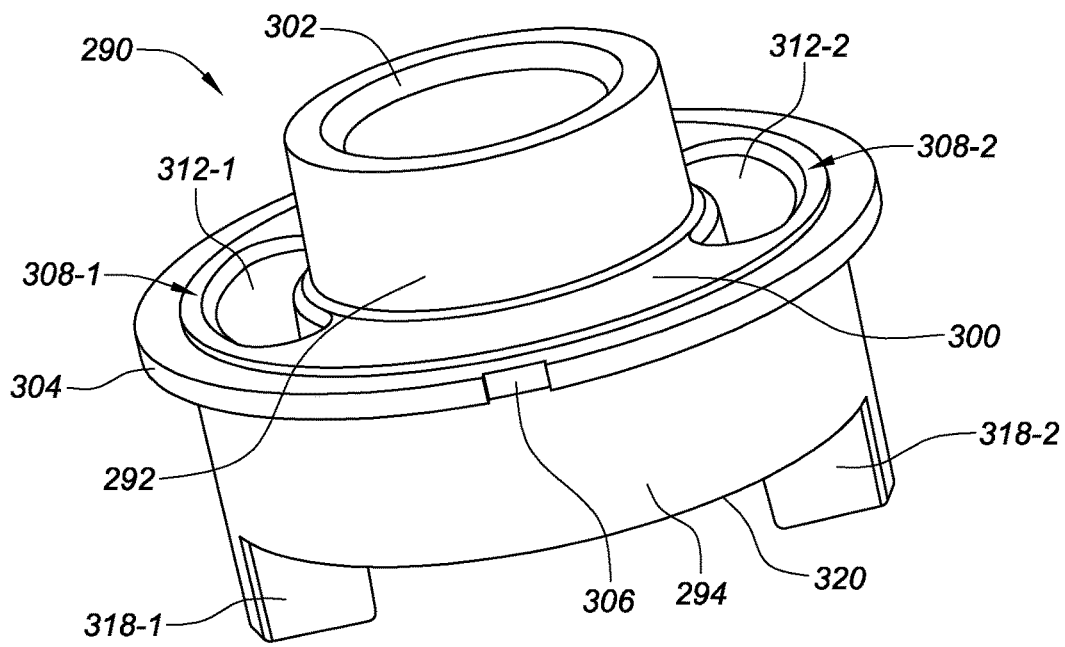
Figure 4C:
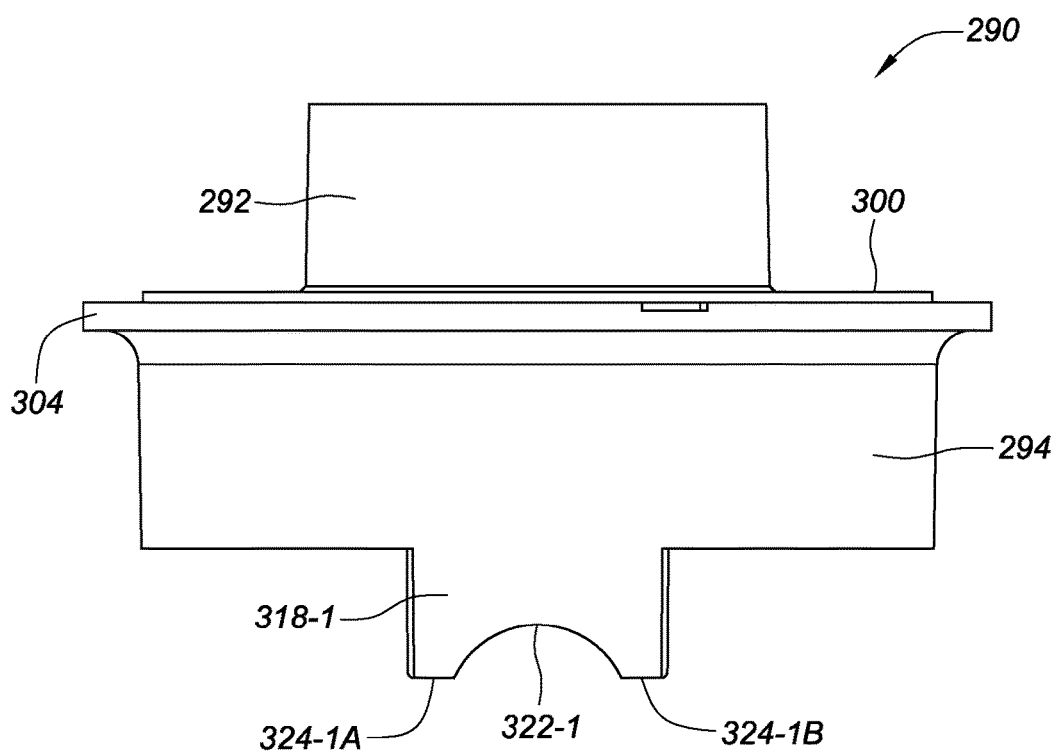
FIG. 4C is a side view of the heater coil housing depicted in FIGS. 4A and 4B.

FIGS. 4A and 4B are isometric side and proximal end views of a heater coil housing 290 of an exemplary e-cigarette and FIG. 4C is a side view of the heater coil housing depicted in FIGS. 4A and 4B. The heater coil housing 290 can include a proximally extending housing neck portion 292 of a first outer diameter and a first inner diameter and a distally extending housing base portion 294 of a second outer diameter and a second inner diameter, each of which are greater than the first outer diameter and the first inner diameter of the proximally extending housing neck portion 292. The proximally extending housing neck portion 292 can extend proximally from a housing face 300 of the heater coil housing 290 and the distally extending housing base portion 294 can extend distally from the housing face 300. In some embodiments, the distal end of the inner tube 142 (FIG. 2C to 2E) can be connected to the proximally extending housing neck portion 292 of the heater coil housing 290. In some embodiments, an outer circumferential surface of the distal end of the inner tube 142 can be connected with an inner circumferential surface of the housing neck portion 292. However, although not depicted, in some embodiments, the outer circumferential surface of the housing neck portion 292 can be connected with an inner circumferential surface of the inner tube 142. In some embodiments, an interface between the distal end of the inner tube 142 and the heater coil housing 290 can form a chamber air outlet 296.

In some embodiments, the housing neck portion 292 can include a tube stop portion 298. The tube stop portion 298 can be a flange that extends radially inward from an inner circumference of the housing neck portion 292. In embodiments, where the outer circumferential surface of the inner tube 142 (FIGS. 2C to 2E) is connected with the inner circumferential surface of the housing neck portion 292, the tube stop portion 298 can prevent the inner tube 142 from being inserted too far into the housing neck portion 292. For example, the inner tube 142 can be pushed into a lumen formed by the housing neck portion 292, until a distal end of the inner tube 142 abuts the tube stop portion 298. In some embodiments, the housing neck portion 292 can include radiused inner proximal edge 302 to help guide the inner tube 142 into the lumen formed by the housing neck portion 292.

With reference to FIG. 4B, the housing base portion 294 can include a flared proximal lip 304, in some embodiments. An outer circumferential surface of the flared proximal lip 304 can be connected with an inner wall of an outer tube 104 (FIGS. 2C to 2E), in some embodiments, which can form a seal between the inner wall of the outer tube 104 and the outer circumferential surface of the flared proximal lip 304, thus preventing liquid from leaking out of the annular liquid storage tank. The flared proximal lip 304 can include an alignment feature 306. In some embodiments, an opposing surface to the flared proximal lip 304 (e.g., an inner surface of the outer tube 104) can include a complementary alignment feature. In some embodiments, the alignment feature 306 and the longitudinally extending grooves 280 (FIGS. 3A and 3B) can be aligned with one another to properly align the heater coil support 250 and the heater coil housing 290.

In some embodiments, the heater coil housing 290 can define a first liquid lumen 308-1 and a second liquid lumen 308-2, configured to provide liquid from the annular liquid storage tank to a wick housed by a heater coil enclosure formed by the heater coil housing 290 and heater coil support, as previously discussed. The first liquid lumen 308-1 can be defined by and longitudinally extend through a first side (e.g., a sidewall) of the heater coil housing 390 and the second liquid lumen 308-2 can be defined by and longitudinally extend through a second side (e.g., sidewall) of the heater coil housing 390, diametrically opposed to the first liquid lumen 308-1. In an example, the first liquid lumen 308-1 and the second liquid lumen 308-2 can be defined by and extend through the housing face 300 and the sidewalls of the distally extending housing base portion 294.

In some embodiments, the first liquid lumen 308-1 and the second liquid lumen 308-2 can be defined by the heater coil housing 290, such that the first liquid lumen 308-1 and the second liquid lumen 308-2 can pass through the heater coil housing 290 parallel to a longitudinal axis of the heater coil housing 290. The first liquid lumen 308-1 and the second liquid lumen 308-2 can provide a passageway from the annular liquid storage tank, as previously discussed, to each end of the wick housed in the heater coil enclosure formed by the heater coil housing 290 and the heater coil support, as further depicted in FIG. 2D. For example, each liquid lumen 308-1, 308-2 can provide liquid to each end of the wick. Thus, liquid can absorb into the wick from either end of the wick.

In some embodiments, a width of each liquid lumen 308-1, 308-2 can change from a proximal side of the liquid lumens 308-1, 308-2 to a distal side of the liquid lumens 308-1, 308-2. For example, the proximal side of the liquid lumens 308-1, 308-2 can define enlarged lumen portions 310-1, 310-2, defined by first and second proximal lumen walls 312-1, 312-2 that extend longitudinally into the sidewalls of the distally extending housing base portion 294. In some embodiments, first and second enlarged lumen portions 310-1, 310-2 can improve a flow of liquid to first and second distal lumen portions 314-1, 314-2. The distal lumen portions 314-1, 314-2 can be defined by first and second distal lumen walls 316-1, 316-2. As depicted, the first and second proximal lumen walls 312-1, 312-2 and the distal lumen walls 316-1, 316-2 can circumferentially extend around a longitudinal axis of the heater coil support 290 and through a portion of the housing face and the sidewalls of the distally extending housing base portion 294.

In some embodiments, the heater coil support 290 can include first and second longitudinally extending wick mounts 318-1, 318-2 that extend distally from a distal surface of the housing base portion 294. In some embodiments, the longitudinally extending wick mounts 318-1, 318-2 can be diametrically opposed to one another. With reference to FIG. 4C, the longitudinally extending wick mount 318-1 can include a first wick support notch 322-1. The second wick mount 318-1 can also include a second wick support notch 322-2, although not shown. The first and second wick support notches 322-1, 322-2 can be complementary to the first and second wick housing notches 278-1, 278-2. First and second wick mount distal ends 324-1A, 324-1B can contact the mount stop portions 282-1, 282-2 (FIG. 3B), thus defining the ports through which the wick extends (e.g., port 234 depicted in FIG. 2E. In some embodiments, in an assembled state, the distally extending housing base portion 294 can be disposed in the support base portion 254 of the heater coil support 250, such that an outer surface of the distally extending housing base portion 294 is connected with an inner surface of the support base portion 254, as depicted in FIGS. 2C to 2D.

In some embodiments, the wick housing notches 278-1, 278-2 (FIG. 3B) and the wick support notches 322-1, 322-2 can together, respectively form the first wick bore 226-1 and the second wick bore 226-2 (FIG. 2D). The first wick bore 226-1 and the second wick bore 226-2 can have a cross-sectional diameter that is less than a diameter of the wick 174. In some embodiments, the smaller diameter can cause the wick 174 to become compressed at first and second end portions of the wick 174, thus holding the wick 174 in place.

Figure 5A:
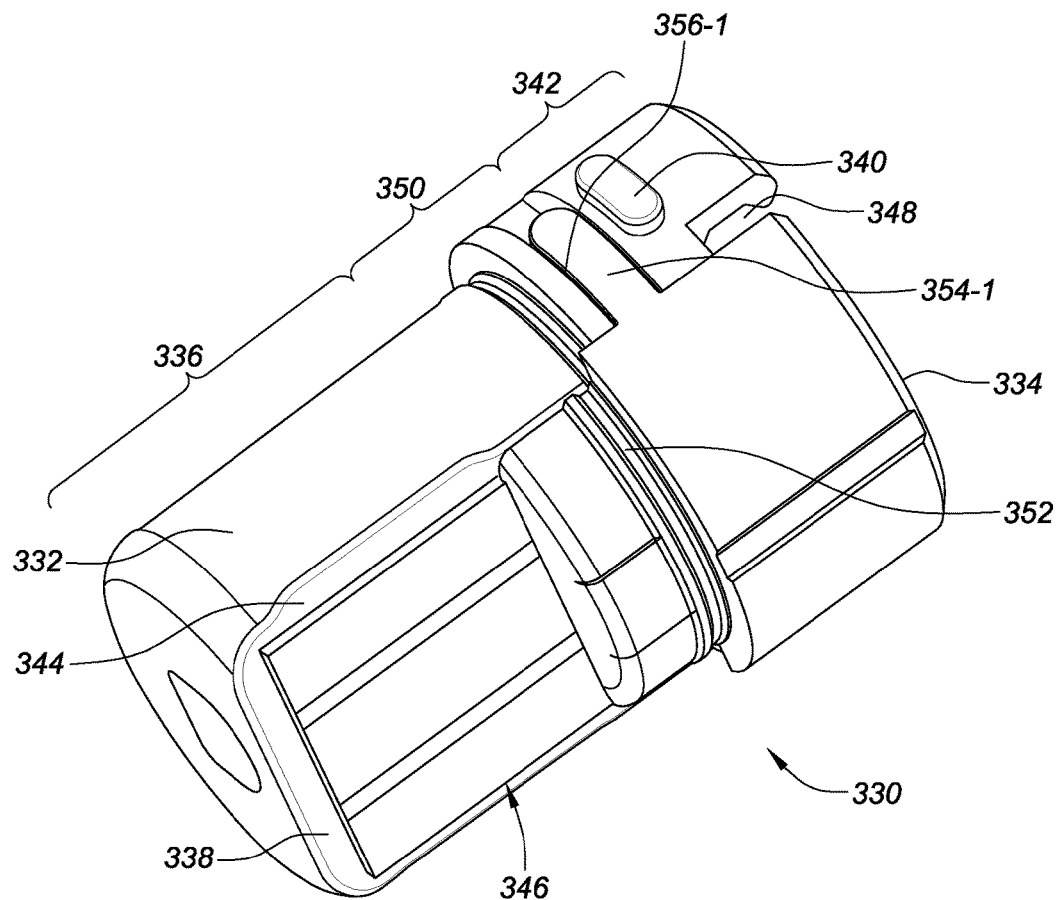
FIG. 5A is an isometric side, top, and distal end view of a battery connector of an exemplary e-cigarette that includes a base connector and a press-fit-connector portion.

FIG. 5A is an isometric side, top, and distal end view of a battery connector of an exemplary e-cigarette that includes a base connector 332 and a press-fit-connector portion 334. The base connector 332 can be a horizontal cylindrical segment, which in some embodiments can be hemi-cylindrical in shape. The base connector 332 can include a contact portion 336 on a distal end of the base connector 332. The contact portion 336 can be a horizontal cylindrical segment, which in some embodiments can be hemi-cylindrical. The contact portion 336 can have an alignment feature 338, which can ensure that the contact portion 336 of the battery connector 330 is inserted with a correct orientation into a complementary connector that comprises the part of the housing for the power supply. The alignment feature 330 can include a flattened circumferential surface of the horizontal cylindrical segment, which forms contact portion 336, in some embodiments. The flattened circumferential surface can provide a mounting location for power, data connections and/or a memory, in some embodiments, as discussed further herein.

In some embodiments, a tube mounting portion 342 and an outer tube of the cartomizer (e.g., outer tube 104) can include a complementary connector, as discussed in relation to FIG. 2B, which in an example can include a radially extending projection 340. In some embodiments, upon insertion of the tube mounting portion 342 into the distal end of the outer tube, the distal end of the outer tube can expand to accommodate the larger diameter tube mounting portion 342. As the tube mounting portion 342 is inserted into the outer tube 104, the tube mounting portion 342 can deflect inward toward the longitudinal axis of the battery connector 330.

As previously discussed, the battery connector 330 can include an alignment feature 338. The alignment feature 338 can include a flattened circumferential surface of the contact portion 336, which can be planar and parallel to a longitudinal axis of the battery connector 330. As further discussed herein, a cross-sectional profile of the contact portion 336 transverse to a longitudinal axis of the battery connector 330 can be D-shaped. In some embodiments, the flattened circumferential surface can include a circuit depression, as previously discussed. In some embodiments, the circuit depression can be defined by a lip 344 extending around a portion of a perimeter of the flattened circumferential surface, which is further discussed herein.

The connector portion 336 can include a connection pad 346, which can be disposed on the flattened circumferential surface. For example, the connector portion 336 can include a connection pad 346, which can be disposed in the circuit depression of the flattened circumferential surface. The connection pad 346 can include an electrical connection, which can serve to provide power to an atomizer and/or other features included in the cartomizer that may require power to operate, and a data connection, which can serve to provide a communication link with various features of the cartomizer, in some embodiments. In some embodiments, the battery connector 330 can include battery connector alignment features (e.g., battery connector alignment feature 348), which can be complementary to one of the first and second support alignment features 258-1, 258-2, as discussed in relation to FIG. 3A. In an example, the battery connector alignment feature 348 can extend distally and longitudinally along the tube mounting portion 342.

In some embodiments, a connection pad can be formed on the flattened circumferential surface of the base connector via laser direct structuring. In an example, the base connector 332 and/or a portion of the base connector that forms the flattened circumferential surface can be formed of a thermoplastic material, which can be doped with a metal-plastic additive. The metal-plastic additive can be activated with a laser. The laser can trace out paths where a trace (e.g., copper trace) is to be formed, by forming nuclei on the path for a subsequent metallization step. In some embodiments, an electroless copper bath can be used to form traces on the paths. In some embodiments, a first connection lead, second connection lead, and/or a data lead like those discussed in relation to FIG. 5B can be formed directly on the flattened circumferential surface of the base connector 332 without the use of a printed circuit board. Accordingly, one or more coil power leads can be connected to the first connection lead and/or the second connection lead, and a memory can be connected to the data lead.

In some embodiments, the battery connector 330 can include a press-fit connector 334. The press-fit connector 334 can include a complementary surface to the flattened circumferential surface of the base connector 332, as previously discussed. In an example, the press-fit connector 334 can be a horizontal cylindrical segment that can include a flattened circumferential surface, which can be complementary to the flattened circumferential surface of the base connector 332. In some embodiments, the press-fit connector 334 can be connected with the base connector 332, such that the flattened circumferential surfaces of the base connector 332 and the press-fit connector 334 can be opposed to one another. The base connector 332 and the press-fit connector 334 can together form the coupling portion 350 and the tube mounting portion 342.

In some embodiments, the base connector 332 and the press-fit connector 334 can define a circumferential groove 352 around the coupling portion 350. In some embodiments, a complementary connector comprising part of or associated with a housing for a power supply can include a circumferential ridge that radially extends from an inner surface of complementary connector and is configured to fit into the circumferential groove 352. In some embodiments, the circumferential ridge and the circumferential groove 352 can fit together to provide a frictional fit between the housing for the power supply and the coupling portion 342.

In some embodiments, the base connector 332 can define a first and second connector groove 356-1, 356-2 that circumferentially extend around a portion of the base connector 332. Additionally, the base connector 332 can define a stepped groove portion 358-1 in the connector groove 356-1. The second connector groove 356-2 can also include a stepped groove portion, although not shown. In some embodiments, the base connector 332 can define a first base alignment pin lumen 360-1 and a second base alignment pin lumen 360-2. The base alignment pin lumens 360-1, 360-2 can be disposed in the flattened circumferential surface of the base connector 332 and can be disposed opposite of one another on the flattened circumferential surface across a longitudinal axis of the base connector 332. In some embodiments, the connection pad 346 can include first and second pad alignment pin lumens 362-1, 362-2, which are disposed opposite of one another on the connection pad 346 and are axially aligned with the base alignment pin lumens 360-1, 360-2 of the base connector 332.

The connection pad 346 can include one or more power leads to which one or more coil power leads (e.g., coil power lead 224) are connected. For example, the connection pad 346 can include a first connection lead 364 and a second connection lead 366. In some embodiments, one of the first connection lead 364 and the second connection lead 366 can be a positive lead and one can be negative lead, which can be electrically coupled to the coil power lead 224 (FIG. 2D) to provide power to the heater coil.

In some embodiments, the connection pad 346 can include a data lead 368 and a memory 370 can be electrically coupled to a proximal end of the data lead 368, as depicted. The memory 370 can be soldered to the data lead 368, in some embodiments. The data lead 368 can electrically couple the memory 370 to a processor included in the power supply portion, in some embodiments. For example, the power supply portion can include a contact pin that electrically couples with the data lead 368. In some embodiments, the press-fit-connector 334 can define a memory slot 372 in a flat circumferential surface 374 of the press-fit connector 334. The press-fit-connector 334 can include a first and second connecting arm 354-1, 354-2 that extend upward from the flattened circumferential surface 374.

In some embodiments, the press-fit connector 334 can be connected to the base connector via the pair of connecting arms 354-1, 354-2. In some embodiments, the connecting arms 354-1, 354-2 can extend upward and radially outward from the flattened circumferential surface 374 to match a curve of the first and second connector grooves 356-1, 356-2 that circumferentially extend around the portion of the base connector 332. Each of the connecting arms 354-1, 354-2 can include a first prong portion 376-1 and a second prong portion 376-2 that each extend from a tip of each connecting arm 354-1, 354-2. In an example, the first prong portion 376-1 can extend from the first connecting arm 354-1 towards the second connecting arm 354-2 and the second prong portion 376-2 can extend from the second connecting arm 354-2 towards the first connecting arm 354-1. In some embodiments, a first alignment pin 378-1 and a second alignment pin 378-2 can extend upward from the flat circumferential surface 374 and can be perpendicular to the flat circumferential surface 374.

FIG. 5B is an isometric side and top view of a base connector 332 of an exemplary e-cigarette with memory 370 and FIG. 5C is an isometric side and bottom view of a press-fit-connector 334 of an exemplary e-cigarette. In some embodiments, the press-fit-connector 334 can be connected with the base connector 332. In connection of the press-fit-connector 334 with the base connector 332, the first alignment pin 378-1 can be disposed in the first pad alignment pin lumen 362-1 and the first base alignment pin lumen 360-1 and the second alignment pin 378-2 can be disposed in the second pad alignment pin lumen 362-2 and the second base alignment pin lumen 360-2. As the press-fit-connector 334 is connected with the base connector 332, the first connecting arm 354-1 and the second connecting arm 354-2 can expand (e.g., flex) radially as the prong portions 376-1, 376-2 of each connecting arm 354-1, 354-2 slides along a respective one of the first and second connector grooves 356-1, 356-2, until the prong portions 376-1, 376-2 become aligned with a respective stepped groove portion (e.g., stepped groove portion 358-1).

To allow the connecting arms 354-1, 354-2 to flex, the press-fit-connector 334 and/or the connecting arms 354-1, 354-2 can be formed from a flexible material, in some embodiments. Upon alignment of the prong portion 376-1 and the stepped groove portion 358-1, the first connecting prong 354-1 can flex inward, causing the prong portion 376-1 to become locked in the stepped groove portion 358-1. Upon connection of the press-fit-connector 334 with the base connector 332, the memory 370 can be disposed in the memory slot 372. The design of the base connector 332 and the press-fit-connector 334 can provide a press-fit connection between the connection pad 346, the base connector 332, and the press-fit-connector 334. As previously discussed, as the tube mounting portion portion 342 of the battery connector 330 is inserted into the distal end of a cartomizer, the press-fit-connector 334 and the base connector 332 can be pressed together. For example, the press-fit-connector 334 and the base connector 332 can both be pressed against the connection pad 346 and the memory 370. In an example, the inner surface of the proximal end of the outer tube forming the cartomizer can press against the tube mounting portion 342, creating a radial force that is directed inwardly toward the longitudinal axis of the tube mounting portion 342. The radial force can be transferred by the base connector 332 and the coupling portion 350 of the press-fit-connector 334 to the connection pad 346 and the memory 370, securely holding the connection pad 346 and the memory 370 in place, between the press-fit-connector 334 and the base connector 332. In some embodiments, the memory 370 can be held in place solely via the memory slot 372 (e.g., without solder), as a result of the connection between the press-fit-connector and the base connector 332 and/or the radial force that is directed inwardly toward the longitudinal axis of the tube mounting portion 342.

In summary, in one aspect the electronic smoking device has an outer tube mounted around at least a portion of an inner tube. The outer tube can comprise an outer surface and an inner surface. The inner tube can comprise an inner surface defining an air path and an outer surface. An annular liquid storage tank is defined between the outer surface of the inner tube and the inner surface of the outer tube. A mouth piece is connected to a proximal end of the inner tube and to the outer tube. A heater enclosure can define a heater coil chamber. A heater coil can be mounted at least partially within the heater enclosure. A wick can include a first end portion. The wick can extend through a center of the heater coil and the first end portion can extend into a first wick bore in a first wall of the heater enclosure. The first end portion of the wick can be in fluid communication with the annular liquid storage tank via a first liquid lumen that extends through the first wall of the heater enclosure.

According to various embodiments, the wick further comprises a second end portion that extends into a second wick bore in a second wall of the heater enclosure, wherein the second end portion of the wick is in fluid communication with the annular liquid storage tank via a second liquid lumen that extends through the second wall of the heater enclosure. According to various embodiments the heater enclosure includes a heater coil housing and a heater coil support; and the first liquid lumen and the second liquid lumen are defined by the heater coil housing. According to various embodiments, the first liquid lumen longitudinally extends through a first side of the heater coil housing and the second liquid lumen longitudinally extends through a second side of the heater coil housing. According to various embodiments, the first liquid lumen is diametrically opposed to the second liquid lumen. According to various embodiments the heater coil housing includes a housing neck portion and a housing base portion, the housing neck portion defining a chamber air outlet. According to various embodiments, the heater coil support includes a support neck portion and a support base portion, the support base portion defining an inlet lumen.

According to various embodiments, a valve grommet is disposed in the inlet lumen, wherein the valve grommet defines a chamber air inlet extending therethrough. According to various embodiments, valve grommet includes an airflow admitter disposed on a distal end of the valve grommet. According to various embodiments, a battery connector connected to a distal end of the support neck portion, the battery connector defining a valve chamber and an air inlet, the valve chamber being in fluid communication with the air inlet and the heater coil chamber. According to various embodiments, a valve ball is disposed in the valve chamber; and a valve opening is defined by the battery connector between the valve chamber and the air inlet, the valve opening having a diameter that is less than a diameter of the valve ball. According to various embodiments, a proximal portion of the first and second liquid lumens includes an enlarged liquid lumen defined by proximal lumen walls that extend longitudinally into the first and second side of the heater coil housing.

In summary, in one aspect the electronic smoking device has a base connector that includes a first horizontal cylindrical segment that extends along a longitudinal axis and defines a first flattened circumferential surface. A connection pad can be disposed on the first flattened circumferential surface and can include a connection lead. A press-fit-connector can comprise a second horizontal cylindrical segment that defines a second flattened circumferential surface. The press-fit-connector can be connected to the base connector such that the second flattened circumferential surface is opposed to the first flattened circumferential surface. The connection pad can be disposed between the first flattened circumferential surface and the second flattened circumferential surface.

According to various embodiments, the connection pad further comprises a data lead and a physical memory electrically coupled with the data lead. According to various embodiments, a memory slot is defined in the second flattened circumferential surface of the press-fit-connector; and the physical memory is disposed in the memory slot. According to various embodiments, the base connector defines an air inlet that extends through the base connector along the longitudinal axis. According to various embodiments, a porous material can be disposed in the air inlet, wherein the porous material comprises an oleophobic coating. According to various embodiments, a one way valve can be disposed in the air inlet.

In summary, in one aspect the electronic smoking device has an outer tube mounted around at least a portion of an inner tube. The outer tube can comprise an outer surface and an inner surface. The inner tube can comprise an inner surface defining an air path and an outer surface. An annular liquid storage tank can be defined between the outer surface of the inner tube and the inner surface of the outer tube. A mouth piece can be connected to a proximal end of the inner tube and to the outer tube. A heater enclosure can define a heater coil chamber. A distal end of the heater enclosure can define a chamber air inlet. A one way valve can be in fluid communication with the heater coil chamber via the chamber air inlet. The one way valve can be configured to allow airflow into the heater coil chamber from the air inlet. A heater coil can be mounted at least partially within the heater enclosure. A wick can include a first end portion and a second end portion. The wick can extend through a center of the heater coil, the first and second end portions being in fluid communication with the annular liquid storage tank.

According to various embodiments, a battery connector can be connected to the distal end of the heater enclosure, the battery connector can define an air inlet lumen, wherein the air inlet lumen is in fluid communication with the heater coil chamber. According to various embodiments, the one way valve can be disposed in the air inlet lumen.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS 10 electronic smoking device
12 end cap
14 power supply portion
16 atomizer/liquid reservoir portion
18 light-emitting diode (LED)
20 air inlets
22 battery
24 control electronics
26 airflow sensor
28 atomizer
30 heating coil
32 wick
34 central passage
36 liquid reservoir
38 air inhalation port
100 cartomizer
102 mouth piece portion
104 outer tube
106 battery connector
108 tube mounting portion
110 contact portion
111 coupling portion
112 alignment feature
113 base connector
114-1 first alignment feature
114-2 second alignment feature
116 air inlet
120 radially extending projection
122 complementary connecter lumen
123 air path
124 flattened circumferential surface
126 circuit depression
128 lip
130 connection pad
132 memory
134 press-fit-connector
136 circumferential groove
140 annular liquid storage tank
142 inner tube
144 mouth piece
146 mouth piece passageway
148 proximal seal
150 heater coil enclosure
152 heater coil chamber 154 heater coil housing
156 heater coil support
158 housing neck portion
160 housing base portion
162-1 first liquid lumen
162-2 second liquid lumen
164 support neck portion
166 support base portion
168 flared proximal lip
170 circumferential support groove
172 circumferential ridge
174 wick
176 heater coil
178 chamber air outlet
180 inlet lumen
182 valve grommet
184 elongate body
186 chamber air inlet
188 proximal flange
190 distal flange
192 airflow admitter
194 longitudinally extending arm
196 arm connector
198 valve ball
200 valve chamber
202 valve opening
204 radiused wall
206 air inlet chamber
208-1 first inner wall
208-2 second inner wall
208-3 third inner wall
210 porous material
220-1 first liquid/wick interface
220-2 second liquid/wick interface
222 airflow admitter aperture
224 coil power lead
226-1 first wick bore
226-2 second wick bore
230-1 first flattened circumferential surface
230-2 second flattened circumferential surface
232 memory slot
234 port
240 D-shaped wall
242 chamfered region
250 heater coil support
252 support neck portion
254 support base portion
256 support groove
258-1 first support alignment feature
258-2 second support alignment feature
260 valve grommet
262 distal flange
264 elongate body
268 chamber air inlet
270-1 first longitudinally extending arm
270-2 second longitudinally extending arm
270-3 third longitudinally extending arm
280 longitudinally extending groove
282-1A mount stop portion
282-2A mount stop portion
290 heater coil housing
292 housing neck portion
294 housing base portion
296 chamber air outlet
298 tube stop portion
300 housing face
302 radiused inner proximal edge
304 flared proximal lip
306 alignment feature
308-1 first liquid lumen
308-2 second liquid lumen
310-1 first enlarged lumen portion
310-2 second enlarged lumen portion
312-1 first proximal lumen wall
312-2 second proximal lumen wall
314-1 first distal lumen portion
314-2 second distal lumen portion
316-1 first distal lumen wall
316-2 second distal lumen wall
318-1 first wick mount
318-2 second wick mount
322-1 first wick support notch
324-1A first wick mount distal end
324-1B second wick mount distal end
330 battery connector
332 base connector
334 press-fit-connector
336 contact portion
338 alignment feature
340 radially extending projection
342 tube mounting portion
344 lip
346 connection pad
348 battery connector alignment feature
350 coupling portion
352 circumferential groove
354-1 first connecting arm
354-2 second connecting arm
356-1 first connector groove
356-2 second connector groove
358-1 first stepped groove portion
358-2 second stepped groove portion
360-1 first base alignment pin lumen
360-2 second base alignment pin lumen
362-1 first pad alignment pin lumen
362-2 second pad alignment pin lumen
364 first connection lead
366 second connection lead
368 data lead
370 memory
372 memory slot
374 flat circumferential surface
376-1 first prong portion
376-2 second prong portion
378-1 first alignment pin
378-2 second alignment pin

The invention claimed is:

1. An electronic smoking device (10), comprising the following:

an outer tube (104) mounted around at least a portion of an inner tube (142), wherein the outer tube (104) comprises an outer surface and an inner surface, wherein the inner tube (142) comprises an inner surface defining an air path (123) and an outer surface, and wherein an annular liquid storage tank (140) is defined between the outer surface of the inner tube (142) and the inner surface of the outer tube (104);

a mouth piece (144) connected to a proximal end of the inner tube (142) and to the outer tube (104);

a heater enclosure (150) defining a heater coil chamber (152); and a heater coil (176) mounted at least partially within the heater enclosure (150); and a wick (174) that includes a first end portion, the wick (174) extending through a center of the heater coil (176) and the first end portion extending into a first wick bore in a first wall of the heater enclosure, wherein the first end portion of the wick (174) is in fluid communication with the annular liquid storage tank (140) via a first liquid lumen (162-1, 308-1) that extends through the first wall of the heater enclosure (150), wherein:
- the wick further comprises a second end portion that extends into a second wick bore in a second wall of the heater enclosure (150), wherein the second end portion of the wick (174) is in fluid communication with the annular liquid storage tank (140) via a second liquid lumen (162-2, 308-2) that extends through the second wall of the heater enclosure (150);
- the heater enclosure (150) includes a heater coil housing (154, 290) and a heater coil support (156, 250); and
- the first liquid lumen (162-1, 308-1) and the second liquid lumen (162-2, 308-2) are defined by the heater coil housing (154, 290).

2. The electronic smoking device (10) of claim 1, wherein:
- the heater enclosure (150) includes a heater coil housing (154, 290) and a heater coil support (156, 250);
- the first liquid lumen (162-1, 308-1) and the second liquid lumen (162-2, 308-2) are defined by the heater coil housing (154, 290); and
- the first liquid lumen (162-1, 308-1) longitudinally extends through a first side of the heater coil housing (154, 290) and the second liquid lumen (162-2, 308-2) longitudinally extends through a second side of the heater coil housing (154, 290).

3. The electronic smoking device (10) of claim 2, wherein the first liquid lumen (162-1, 308-1) is diametrically opposed to the second liquid lumen (162-2, 308-2).

4. The electronic smoking device (10) of claim 1, wherein the heater coil housing (154, 290) includes a housing neck portion (158, 292) and a housing base portion (160, 294), the housing neck portion (158, 292) defining a chamber air outlet (296).

5. The electronic smoking device (10) of claim 1, wherein the heater coil support (156, 250) includes a support neck portion (164, 252) and a support base portion (166, 254), the support base portion (166, 254) defining an inlet lumen (180).

6. The electronic smoking device (10) of claim 5, further comprising a valve grommet (182) disposed in the inlet lumen, wherein the valve grommet (182) defines a chamber air inlet (186) extending therethrough.

7. The electronic smoking device (10) of claim 6, wherein the valve grommet (182) includes an airflow admitter (192) disposed on a distal end of the valve grommet (182).

8. The electronic smoking device (10) of claim 7, further comprising a battery connector (106, 348) connected to a distal end of the support neck portion (164, 252), the battery connector (106, 348) defining a valve chamber (200) and an air inlet (116), the valve chamber (200) being in fluid communication with the air inlet (116) and the heater coil chamber (152).

9. The electronic smoking device (10) of claim 8, wherein:
- a valve ball (198) is disposed in the valve chamber (200); and
- a valve opening (202) is defined by the battery connector (106, 348) between the valve chamber (200) and the air inlet (116), the valve opening (202) having a diameter that is less than a diameter of the valve ball (198).

10. The electronic smoking device (10) of claim 1, wherein a proximal portion of the first and second liquid lumens (162-1, 162-2, 308-1, 308-2) includes an enlarged liquid lumen defined by proximal lumen walls (312-1, 312-2) that extend longitudinally into the first and second side of the heater coil housing (154, 290).

11. A battery connector (106, 330) for an electronic smoking device (10), comprising:
- a base connector (113, 332) comprising a first horizontal cylindrical segment that extends along a longitudinal axis and defines a first flattened circumferential surface (124);
- a connection pad (130, 346) disposed on the first flattened circumferential surface (124), wherein the connection pad includes a connection lead (364, 366); and
- a press-fit-connector (134, 334) comprising a second horizontal cylindrical segment that defines a second flattened circumferential surface (230-1, 230-2), wherein:
  - the press-fit-connector (134, 334) is connected to the base connector (113, 332) such that the second flattened circumferential surface (230-1, 230-2) is opposed to the first flattened circumferential surface (124);
  - the connection pad (130, 346) is disposed between the first flattened circumferential surface (124) and the second flattened circumferential surface (230-1, 230-2); and
  - the connection pad (130, 346) further comprises a data lead (368) and a physical memory (132, 370) electrically coupled with the data lead (368).

12. The battery connector (106, 330) of claim 11, wherein:
- a memory slot (232, 373) is defined in the second flattened circumferential surface (230-1, 230-2) of the press-fit-connector (134, 334); and
- the physical memory (132, 370) is disposed in the memory slot (232, 373).

13. The battery connector (106, 330) of claim 11, wherein the base connector (113, 332) defines an air inlet (116) that extends through the base connector (113, 332) along the longitudinal axis.

14. The battery connector (106, 330) of claim 13, further comprising a porous material (210) disposed in the air inlet (116).

15. The battery connector (106, 330) of claim 14, wherein the porous material (210) comprises an oleophobic coating.

16. An electronic smoking device (10), comprising the following:
- an outer tube (104) mounted around at least a portion of an inner tube (142), wherein the outer tube (104) comprises an outer surface and an inner surface, wherein the inner tube (142) comprises an inner surface defining an air path (123) and an outer surface, and wherein an annular liquid storage tank (140) is defined between the outer surface of the inner tube (142) and the inner surface of the outer tube (104);
- a mouth piece (144) connected to a proximal end of the inner tube (142) and to the outer tube (104);
- a heater enclosure (150) defining a heater coil chamber (152), wherein a distal end of the heater enclosure (150) defines a chamber air inlet (186, 268);
- a one way valve in fluid communication with the heater coil chamber (152) via the chamber air inlet (186, 268), wherein the one way valve is configured to allow airflow into the heater coil chamber (152) from the air inlet (186, 268);

a heater coil (176) mounted at least partially within the heater enclosure (150);

a wick (174) that includes a first end portion and a second end portion, the wick (174) extending through a center of the heater coil (176), the first and second end portions being in fluid communication with the annular liquid storage tank (140); and a battery connector (106, 348) connected to the distal end of the heater enclosure (150), the battery connector (106, 348) defining an air inlet lumen (116), wherein the air inlet lumen (116) is in fluid communication with the heater coil chamber (150).

17. The electronic smoking device (10) of claim 16, wherein the one way valve is disposed in the air inlet lumen (116).

* * * * *